US006364666B1

(12) United States Patent
Jenkins et al.

(10) Patent No.: US 6,364,666 B1
(45) Date of Patent: Apr. 2, 2002

(54) METHOD FOR ADAPTIVE TRAINING OF LISTENING AND LANGUAGE COMPREHENSION USING PROCESSED SPEECH WITHIN AN ANIMATED STORY

(75) Inventors: William M. Jenkins, Pacifica; Michael M. Merzenich, San Francisco; Steven L. Miller, Pacifica; Bret E. Peterson, Lafayette, all of CA (US); Paula Tallal, Lumberville, PA (US)

(73) Assignee: Scientific Learning Corp., Oakland, CA (US)

( * ) Notice: Subject to any disclaimer, the term of this patent is extended or adjusted under 35 U.S.C. 154(b) by 0 days.

(21) Appl. No.: 09/106,947

(22) Filed: Jun. 30, 1998

Related U.S. Application Data

(63) Continuation-in-part of application No. 08/982,189, filed on Dec. 17, 1997, now Pat. No. 5,927,988.

(51) Int. Cl.[7] .............................................. G09B 19/00
(52) U.S. Cl. ...................................... 434/156; 434/185
(58) Field of Search ....................... 364/710.03; 600/23, 600/24; 434/112, 116, 128, 129, 156, 167, 185

(56) References Cited

U.S. PATENT DOCUMENTS

| | | | | |
|---|---|---|---|---|
| 4,594,686 A | * | 6/1986 | Yoshida .................. 434/156 X |
| 5,169,342 A | * | 12/1992 | Steele et al. ................ 434/112 |
| 5,395,242 A | * | 3/1995 | Slye et al. ............... 434/128 X |
| 5,791,904 A | * | 8/1998 | Russell et al. ........... 434/167 X |
| 5,813,862 A | * | 9/1998 | Merzenich et al. .......... 434/185 |
| 5,870,709 A | * | 2/1999 | Bernstein ................. 434/156 X |
| 5,885,083 A | * | 3/1999 | Ferrell ......................... 434/156 |

OTHER PUBLICATIONS

Temporal Processing Deficits of Language–Learning Impaired Children Ameliorated by Training, by Merzenich, Jenkins, Johnston, Schreiner, Miller & Tallal, Science Magazine, vol. 271, Jan. 5, 1996.

* cited by examiner

*Primary Examiner*—Sam Rimell
(74) *Attorney, Agent, or Firm*—James W. Huffman

(57) ABSTRACT

A method for adaptively training a subject, using auditory processing of phonemes within command sentences, to improve the subject's listening comprehension, grammatical parsing, and serial memory is provided. The method utilizes a number of training installments, each designed for testing a particular aspect of the subject's language skills, all tied together by a common story. More specifically, installments are provided that narrate a story, test the subject's listening comprehension to the narrated story, test the subject's ability to grammatically parse increasingly difficult sentence structures, and test the subject's ability to select and manipulate graphical objects in response to auditory commands. Speech processing is used for the narration, as well as for commands within each test to allow the subject to more easily distinguish between similar sounding phonemes. As the subject improves his/her ability to correctly respond to the tests, the amount of processing applied to the commands is reduced, ultimately to the level of normal speech.

29 Claims, 10 Drawing Sheets

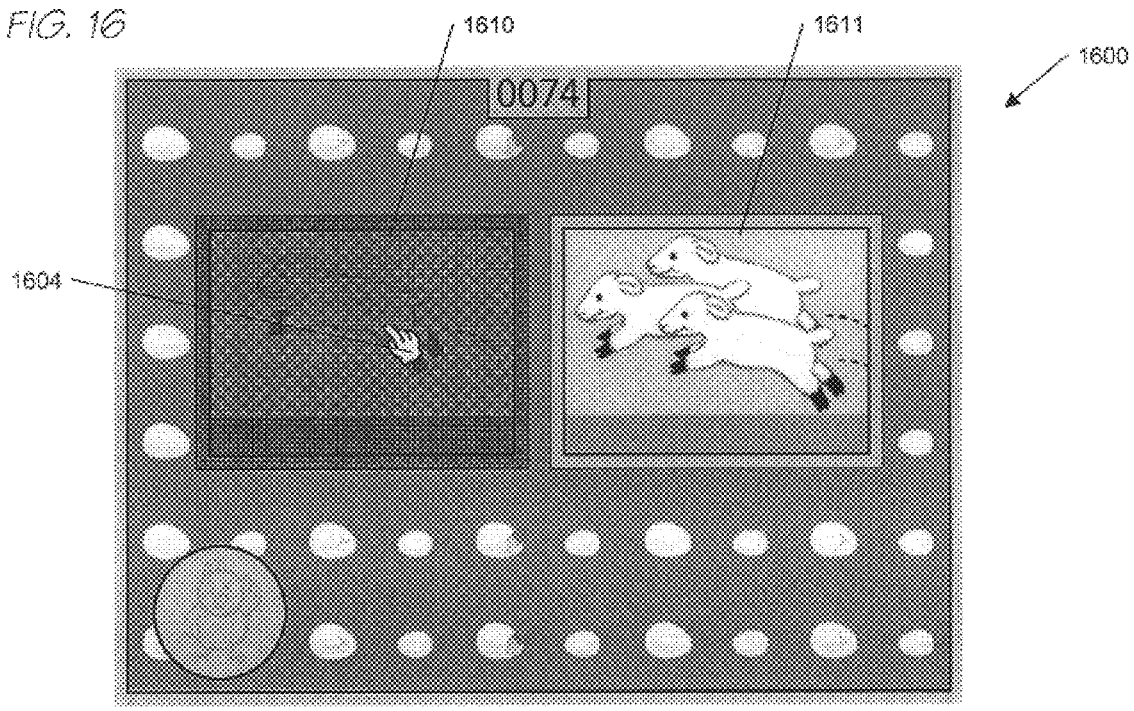
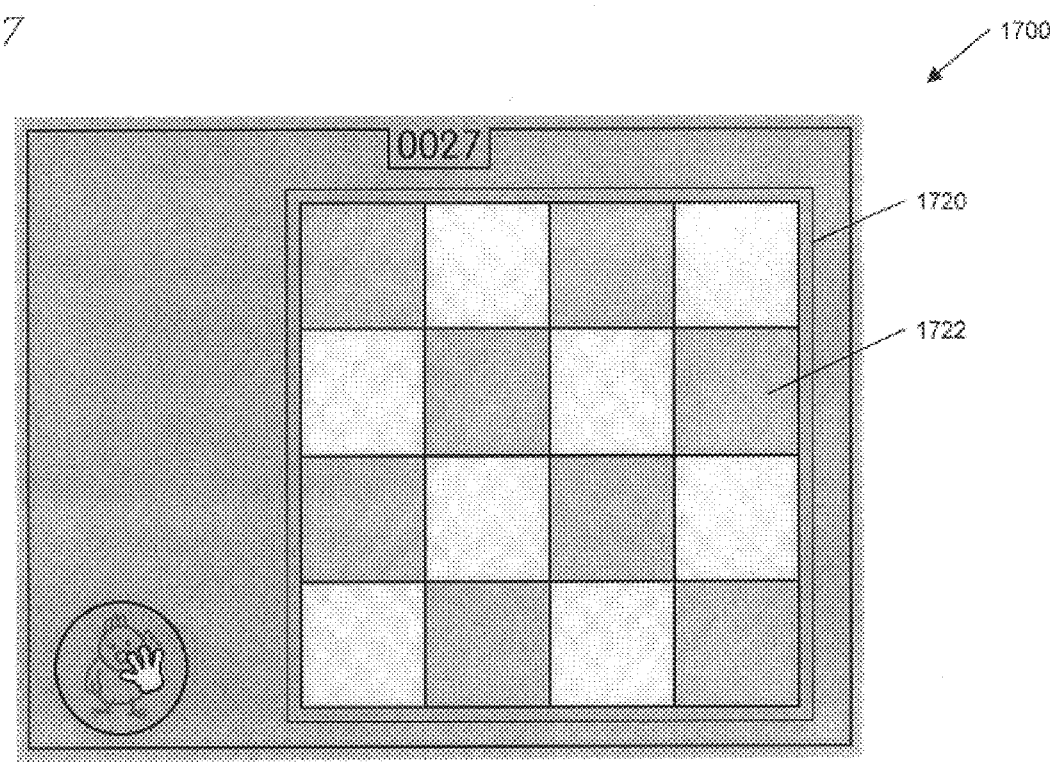

METHOD FOR ADAPTIVE TRAINING OF LISTENING AND LANGUAGE COMPREHENSION USING PROCESSED SPEECH WITHIN AN ANIMATED STORY

CROSS REFERENCE TO RELATED APPLICATIONS

This application is a Continuation-in-Part of U.S. patent application Ser. No. 08/98,189 filed Dec. 17, 1997, now U.S. Pat. No. 5,927,988 entitled "METHOD AND APPARATUS FOR TRAINING OF SENSORY AND PERCEPTUAL SYSTEMS IN LLI SUBJECTS"; and is related to U.S. patent application Ser. No. 08/992071, filed Dec. 17, 1997, entitled "METHOD AND APPARATUS FOR TRAINING OF SENSORY AND PERCEPTUAL SYSTEMS IN LLI SUBJECTS"; and U.S. patent application Ser. No. 08/992072, filed Dec. 17, 1997 entitled "METHOD AND APPARATUS FOR TRAINING OF COGNITIVE AND MEMORY SYSTEMS IN HUMANS"; both assigned to Scientific Learning Corporation.

BACKGROUND OF THE INVENTION

1. Field of the Invention

This invention relates in general to the field of language education, and more specifically to a computer program for training a human's auditory processing system to discriminate between and accurately identify similarly sounding phonemes or words, and to associate representative graphemes with the phonemes or words.

2. Description of the Related Art

Up to ten percent of children have language-learning impairments (LLI) resulting from the inability to accurately process short duration acoustic events at the rates that occur in normal speech. Their trouble distinguishing among elements of speech is neurologically based and has far reaching consequences, including: academic failure, emotional and disciplinary problems, and possibly diminished lifelong achievement and self-image. No bracket of intelligence, race, gender or economic level is immune from this problem.

More specifically, Children with LLI have difficulty detecting and identifying sounds that occur simultaneously or in close proximity to each other—a phenomenon known as "masking." Because of masking, children with LLI require sounds that are as much as 45 decibels more intense than a preceding or subsequent masking noise to distinguish and understand them. In addition, children with LLI are consistently poorer at detecting a brief tone presented with a masking noise, particularly when the brief tone is turned on immediately prior to the masking noise. This phenomenon is called "backward masking." Similarly, when the brief tone is turned on immediately after the masking noise a similar decrease in detectability can occur. This phenomenon is called "forward masking". For a tone to be detected by a child with LLI in the presence of a masking noise, the tone must be separated in time or frequency from the masking noise.

The inability to accurately distinguish and process short duration sounds often causes children to fall behind in school. Since the children can't accurately interpret many language sounds, they can't remember which symbols represent which sounds. This deficiency causes difficulties in learning to read (translating from symbols to sounds), and in spelling. In fact, it is common for a child with LLI to fall two to three years behind his/her peers in speech, language and reading development.

One way children develop such auditory processing problems is from middle ear infections when they are young and beginning to develop the oral representations of language in the central auditory nervous system. When a child has an ear infection, fluid can build up and block or muffle the sound wave entering the ear causing intermittent hearing loss. Even if the infection doesn't permanently damage the ear, the child's brain doesn't learn to process some sounds because it hasn't heard them accurately before, on a consistent basis. This typically occurs during a critical period of brain development when the brain is building the nerve connections necessary to accurately process acoustic events associated with normal speech.

Researchers believe that the auditory processing problem is essentially one of timing. Vowel sounds like /a/ and /e/ usually last at least 100 milliseconds and typically have constant frequency content. Consonants, on the other hand, typically have modulated frequency components, and last less than 40 milliseconds. Children with LLI cannot process these faster speech elements, especially the hard consonants like /t/, /p/, /d/ and /b/, if they occur either immediately before or after vowels, or if they are located near other consonants. Rather than hearing the individual sounds that make up a particular phoneme, children with LLI integrate closely associated sounds together over time. Since the duration of vowels are typically longer than consonants, the modulated frequency portions of consonants are often lost in the integration, an affect that may also hinder the resolution of the vowel, particularly short duration vowels.

This problem of abnormal temporal integration of acoustic events over time is not limited to children with LLI. Rather, the problem extends to stroke victims who have lost the neurological connections necessary to process speech, as well as to individuals raised in one country, having one set of language phonemes, and attempting to learn the language of another country, having a distinct set of language phonemes. For example, it is known that an individual raised in Japan is not often presented with phonemes similar to the English r's and l's, because those consonants are not common in the Japanese language. Similarly, there are many subtleties in the sounds made by a speaker of Japanese that are difficult to distinguish unless raised in Japan. The phonetic differences between languages are distinctions that must be learned, and are often very difficult. But, they are clearly problems that relate to the temporal processing of short duration acoustic events.

The above described temporal processing deficiency has little if anything to do with intelligence. In fact, some LLI specialists argue that brains choosing this different route by which to absorb and reassemble bits of speech may actually stimulate creative intelligence, but at the expense of speech and reading problems.

Recent studies have shown that if the acoustic events associated with phonemes that are difficult to distinguish, such as /ba/ and /da/, are slowed down, or that the consonant portion of the phonemes are emphasized, that students diagnosed as LLI can accurately distinguish between the phonemes. In addition, if the interval between two complex sounds is lengthened, LLI students are better able to process the sounds distinctly.

Heretofore, the solution to the processing problem has been to place LLI students in extended special education and/or speech therapy training programs that focus on speech recognition and speech production. Or, more commonly, repetitive reading programs, phonic games, or other phonic programs are undertaken. These programs often last for years, with a success rate that is often more closely associated with the skill of the speech and language professional than with the program of study.

What is needed is a method and apparatus that allows a subject with abnormal temporal processing to train, or retrain their brain to recognize and distinguish short duration acoustic events that are common in speech. Moreover, what is needed is a program that repetitively trains a subject to distinguish phonemes at a normal rate, by emphasizing elements of speech to the point that they are distinguishable, and then adaptively adjusting the emphasis of the speech elements to the level of normal speech. The adaptive adjustments should be made so as to encourage the subject to continue with the repetitions, and the number of repetitions should be sufficient to develop the necessary neurological connections for normal temporal processing of speech. Moreover, the program should provide acoustic signals to the brain that are better for phonetic training than normal human speech.

Furthermore, what is needed is a program that trains a subject to discriminate between similar phonemes in increasingly complex situations (i.e., identifying sounds at the beginning, middle and end of words), to identify sequences of stimuli that are delivered in rapid succession (i.e., at speeds common in normal speech), and to begin associating phonemes with particular graphic representations (graphemes).

SUMMARY

To address the above-detailed deficiencies, the present invention provides a method for adaptively training a subject's listening comprehension using processed speech. The method includes: presenting a visual story to the subject, accompanied with an auditory narration, the auditory narration being played using a speech processing; presenting questions to the subject that are related to the presented story, the questions having visual and auditory components, the auditory components using speech processing; and the story and questions for different speech processing levels.

In another aspect, the present invention provides a method for training a subject's language comprehension by using an animated story, the animated story having visual and auditory components, the auditory components processed according to different speech processing levels. The method includes: providing different skill levels for training the subject, the skill levels having a different questions; presenting a question to the subject, the question having a visual component and an auditory component, the auditory component processed according to one of the speech processing levels; repeating presentation of a question; and when the subject reaches a predetermined correct response threshold, changing the speech processing level used to process the auditory component of a question.

In yet another aspect, the present invention provides a method for adaptively training a subject's serial order command comprehension by using an animated story, the animated story having visual and auditory components, the auditory components processed according to different speech processing levels. The method includes: providing categories for training the subject's serial order comprehension, the categories having selection/manipulation commands; providing graphical objects that may be selected or manipulated by the subject, the graphical objects associated with the animated story; playing the selection/manipulation commands, the commands auditorily processed according by the different of speech processing levels; requiring the subject to select or manipulate the graphical objects according to the played selection/manipulation commands; and repeating the above for each of the provided categories.

In a further aspect, the present invention provides a method for improving a subject's comprehension of spoken language using processed speech within a plurality of animated stories. The method includes: providing selection/manipulation games, each of the games having a questions or commands related to animated stories, each of the questions or commands having visual and auditory components, the auditory components processed by different speech processing levels; narrating at least a portion of one of the animated stories, the narration having graphical animations and speech processed according to one of the plurality of speech processing levels; presenting the questions or commands for the selection/manipulation games, the auditory components of the presented questions or commands processed according to the different speech processing levels; when a subject correctly responds to the questions or commands according to a predetermined threshold, repeating the narration and questions for a different animated story using a different speech processing level.

BRIEF DESCRIPTION OF THE DRAWINGS

These and other objects, features, and advantages of the present invention will become better understood with regard to the following description, and accompanying drawings where:

FIG. 16 is a pictorial representation of a game screen illustrating incorrect response to a trial within the game Language Comprehension.

FIG. 17 is a pictorial representation of an initial game screen for the Block Commander game within Start-Up Stories.

DETAILED DESCRIPTION

Figure 1:
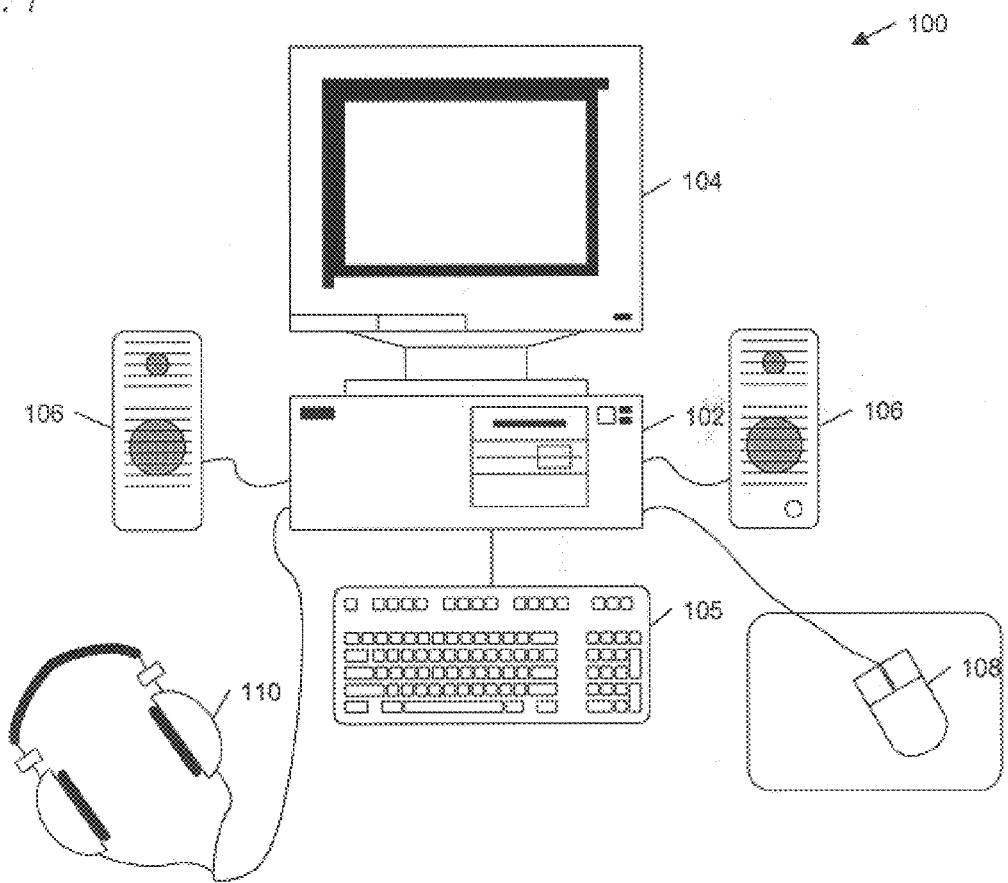
FIG. 1 is a block diagram of a computer system for executing a program according to the present invention.

Referring to FIG. 1, a computer system 100 is shown for executing a computer program to train, or retrain a subject, according to the present invention. The computer system 100 contains a computer 102, having a CPU, memory, hard disk and CD ROM drive (not shown), attached to a monitor 104. The monitor 104 provides visual prompting and feedback to the subject during execution of the computer program. Attached to the computer 102 are a keyboard 105, speakers 106, a mouse 108, and headphones 110. The speakers 106 and the headphones 110 provide auditory prompting and feedback to the subject during execution of the computer program. The mouse 108 allows the subject to navigate through the computer program, and to select particular responses after visual or auditory prompting by the computer program. The keyboard 105 allows an instructor to enter alpha numeric information about the subject into the computer 102. Although a number of different computer platforms are applicable to the present invention, embodiments of the present invention execute on either IBM compatible computers or Macintosh computers.

Figure 2:
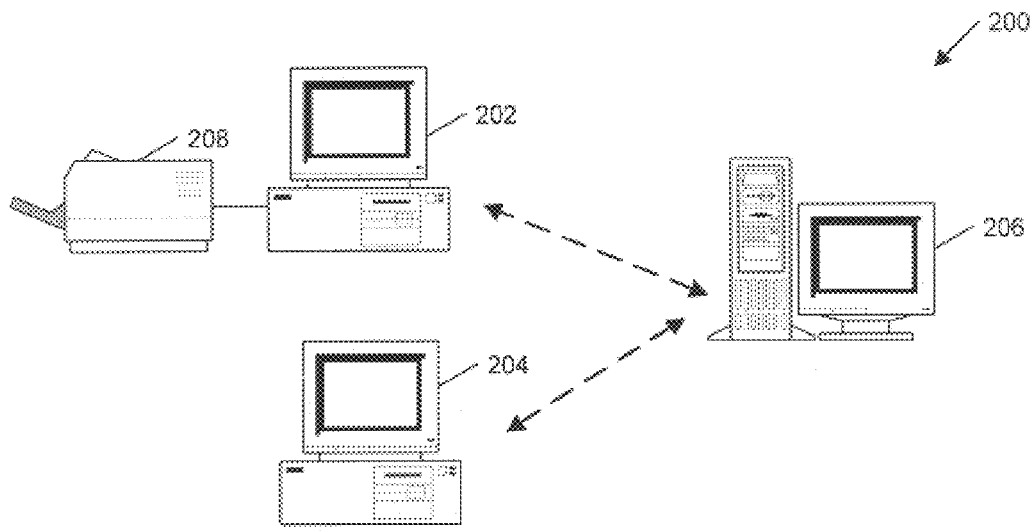
FIG. 2 is a block diagram of a computer network for executing a program according to the present invention.

Now referring to FIG. 2, a computer network 200 is shown. The computer network 200 contains computers 202, 204, similar to that described above with reference to FIG. 1, connected to a server 206. The connection between the computers 202, 204 and the server 206 can be made via a local area network (LAN), a wide area network (WAN), or via modem connections, directly or through the Internet. A printer 208 is shown connected to the computer 202 to illustrate that a subject can print out reports associated with the computer program of the present invention. The computer network 200 allows information such as test scores, game statistics, and other subject information to flow from a subject's computer 202, 204 to a server 206. An administrator can then review the information and can then download configuration and control information pertaining to a particular subject, back to the subject's computer 202, 204.

Before providing a detailed description of the present invention, a brief overview of certain components of speech will be provided, along with an explanation of how these components are processed by LLI subjects. Following the overview, general information on speech processing will be provided so that the reader will better appreciate the novel aspects of the present invention.

Figure 3:
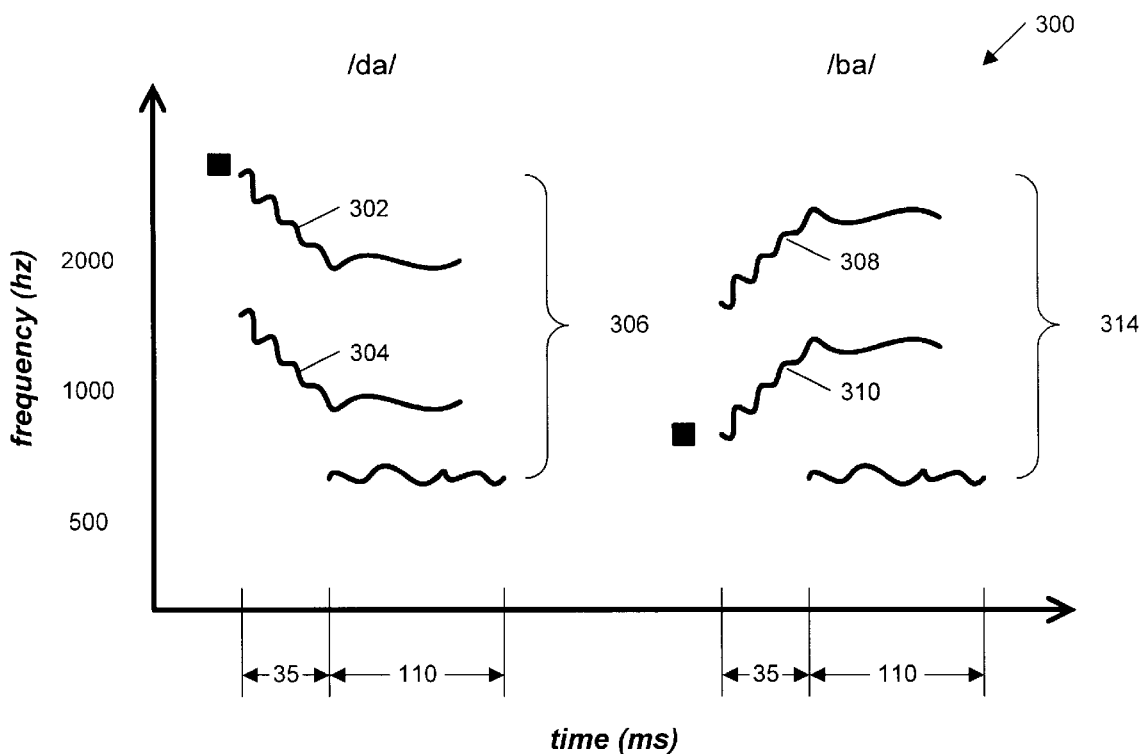
FIG. 3 is a chart illustrating frequency/energy characteristics of two phonemes within the English language.

Referring to FIG. 3, a chart is shown that illustrates frequency components, over time, for two distinct phonemes within the English language. Although different phoneme combinations are applicable to illustrate features of the present invention, the phonemes /da/ and /ba/ are shown. For the phoneme /da/, a downward sweep frequency component 302, at approximately 2.5–2 khz is shown to occur over a 35 ms interval. In addition, a downward sweep frequency component 304, at approximately 1 khz is shown to occur during the same 35 ms interval. At the end of the 35 ms interval, constant frequency components 306 are shown, whose duration is approximately 110 ms. Thus, in producing the phoneme /da/, the stop consonant portion of the element /d/ is generated, having high frequency sweeps of short duration, followed by a long vowel element /a/ of constant frequency.

Also shown are frequency components for a phoneme /ba/. This phoneme contains an upward sweep frequency component 308, at approximately 2 khz, having a duration of approximately 35 ms. The phoneme also contains an upward sweep frequency component 310, at approximately 1 khz, during the same 35 ms period. Following the stop consonant portion /b/ of the phoneme, are constant frequency vowel portions 314 whose duration is approximately 110 ms.

Thus, both the /ba/ and /da/ phonemes begin with stop consonants having modulated frequency components of relatively short duration, followed by a constant frequency vowel components of longer duration. The distinction between the phonemes exists primarily in the 2 khz sweeps during the initial 35 ms interval. Similarity exists between other stop consonants such as /ta/, /pa/, /ka/ and /ga/.

Figure 4:
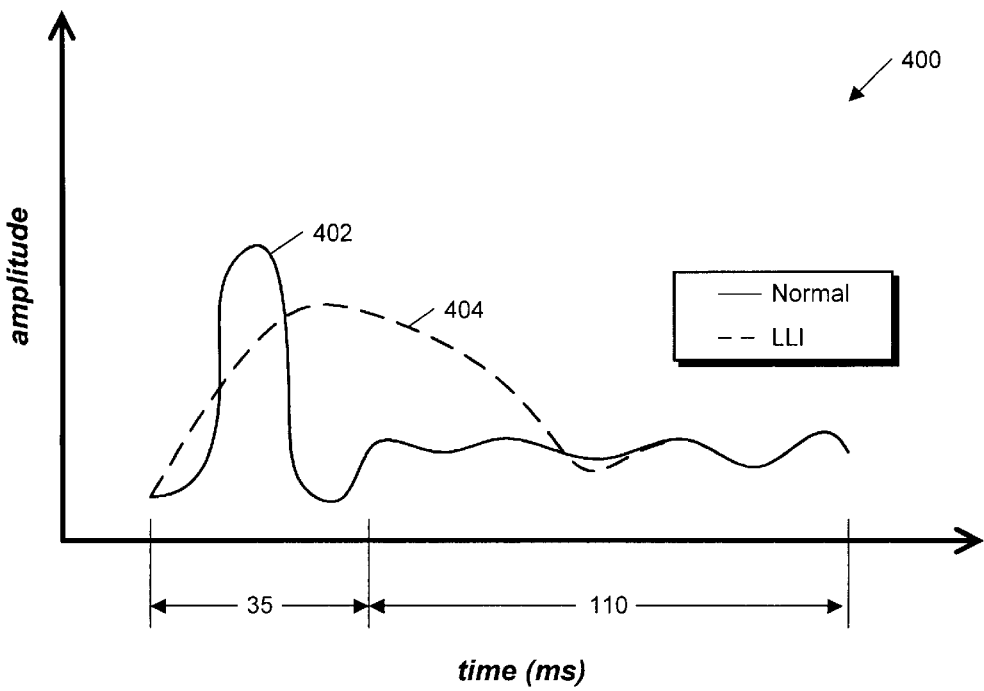
FIG. 4 is a chart illustrating auditory reception of a phoneme by a subject having normal receptive characteristics, and by a subject whose receptive processing is impaired.

Referring now to FIG. 4, the amplitude of a phoneme, for example /ba/, is viewed in the time domain. A short duration high amplitude peak waveform 402 is created upon release of either the lips or the tongue when speaking the consonant portion of the phoneme, that rapidly declines to a constant amplitude signal of longer duration. For an individual with normal temporal processing, the waveform 402 will be understood and processed essentially as it is. However, for an individual who is learning-language impaired, or who has abnormal temporal processing, the short duration, higher frequency consonant burst will be integrated over time with the lower frequency vowel, and depending on the degree of impairment, will be heard as the waveform 404. The result is that the information contained in the higher frequency sweeps associated with consonant differences, will be muddled, or indistinguishable.

With the above general background of speech elements, and how LLI subjects process them, a general overview of speech processing will now be provided. As mentioned above, one problem that exists in LLI subjects is the inability to distinguish between short duration acoustic events. If the duration of these acoustic events is stretched, in the time domain, it is possible to train LLI subjects to distinguish between these acoustic events. An example of such time domain stretching is shown in FIG. 5, to which attention is now directed.

Figure 5:
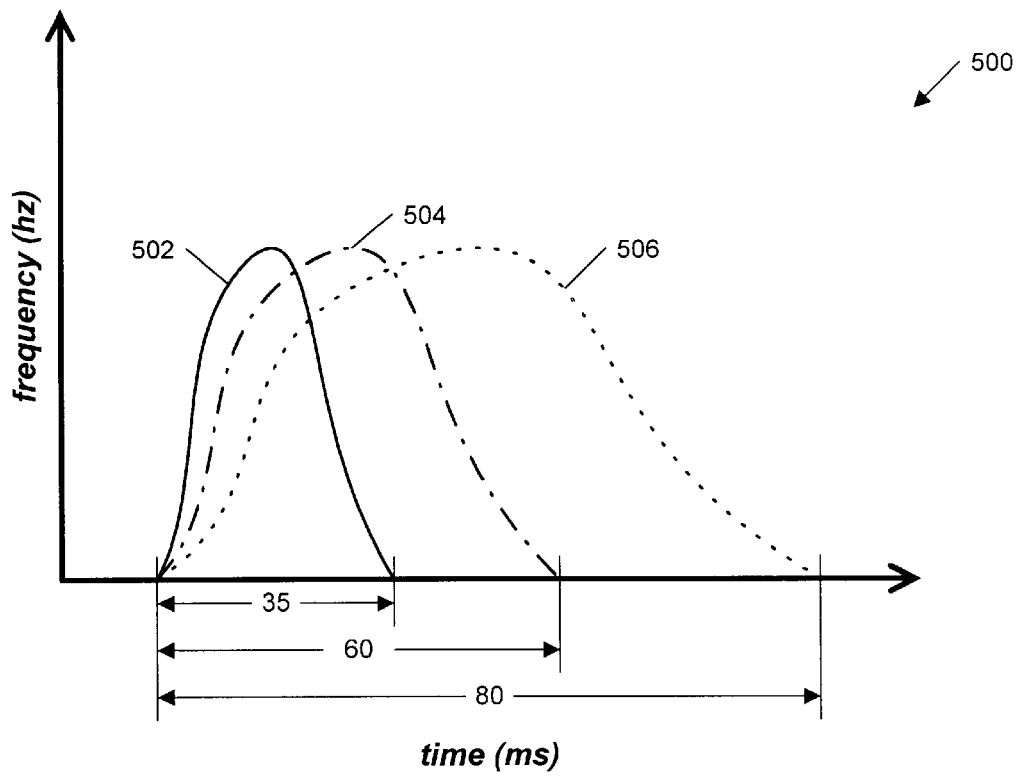
FIG. 5 is a chart illustrating stretching of a frequency envelope in time, according to the present invention.

In FIG. 5, a frequency vs. time graph 500 is shown that illustrates a waveform 502 having short duration characteristics similar to the waveform 402 described above. Using existing computer technology, the analog waveform 502 can be sampled and converted into digital values. The values can then be manipulated so as to stretch the waveform in the time domain to a predetermined length, while preserving the amplitude and frequency components of the modified waveform. The modified waveform can then be converted back into an analog waveform for reproduction by a computer, or by some other audio device. The waveform 502 is shown stretched in the time domain to durations of 60 ms (waveform 504), and 80 ms (waveform 506). By stretching the consonant portion of the waveform 502 without effecting its frequency components, subjects with LLI can begin to hear distinctions in common phonemes.

Figure 6:
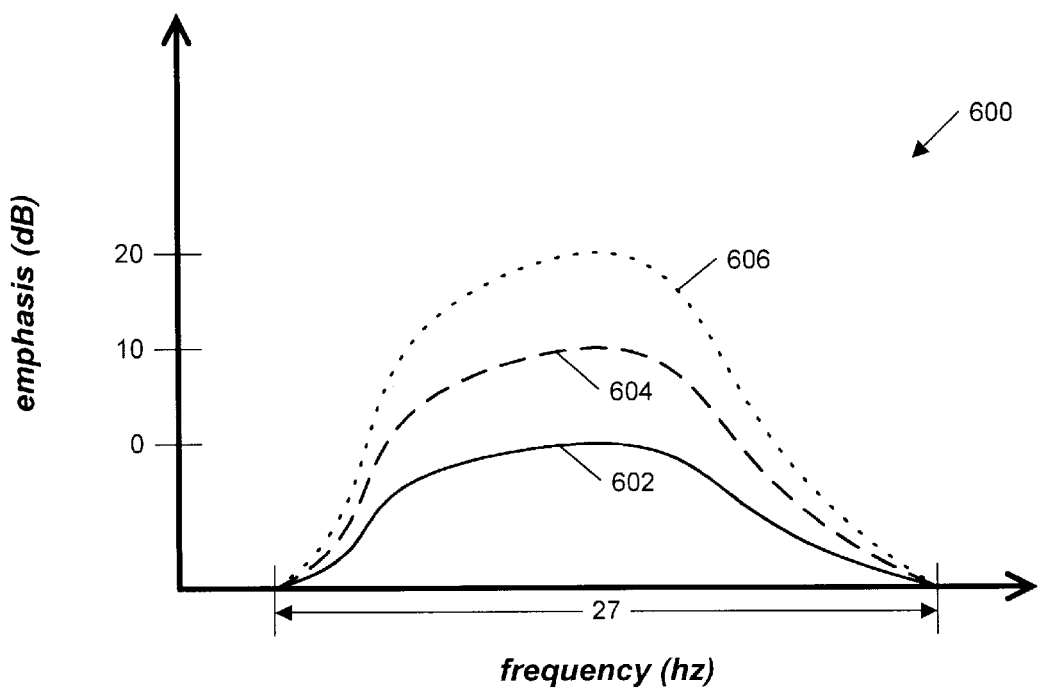
FIG. 6 is a chart illustrating emphasis of selected frequency components, according to the present invention.

Another method that may be used to help LLI subjects distinguish between phonemes is to emphasize selected frequency envelopes within a phoneme. Referring to FIG. 6, a graph 600 is shown illustrating a frequency envelope 602 whose envelope varies by approximately 27 hz. By detecting frequency modulated envelopes that vary from say 3–30 hz, similar to frequency variations in the consonant portion of phonemes, and selectively emphasizing those envelopes, they are made more easily detectable by LLI subjects. A 10 dB emphasis of the envelope 602 is shown in waveform 604, and a 20 dB emphasis in the waveform 606.

Figure 7:
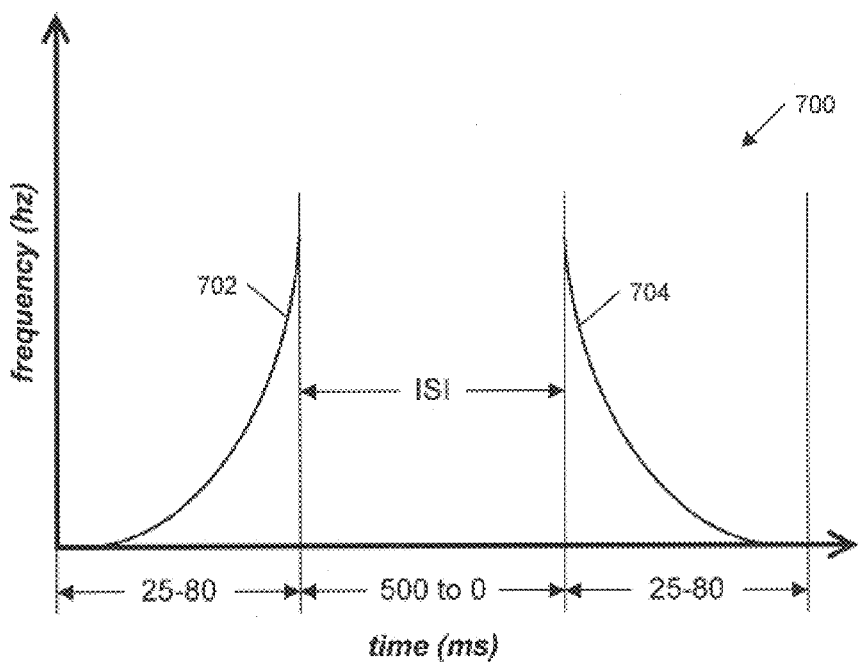
FIG. 7 is a chart illustrating up-down frequency sweeps of varying duration, separated by a selectable inter-stimulus-interval (ISI), according to the present invention.

A third method that may be used to train LLI subjects to distinguish short duration acoustic events is to provide frequency sweeps of varying duration, separated by a predetermined interval, as shown in FIG. 7. More specifically, an upward frequency sweep 702, and a downward frequency sweep 704 are shown, having duration's varying between 25 and 80 milliseconds, and separated by an interstimulus interval (ISI) of between 500 and 0 milliseconds. The duration and frequency of the sweeps, and the interstimulus interval between the sweeps are varied depending on the processing level of the LLI subject, as will be further described below.

Utilization of up-down frequency sweeps with varying ISI has been fully described in U.S. patent application No. 08/858961, entitled "METHOD AND DEVICE FOR ENHANCING THE RECOGNITION OF SPEECH AMONG SPEECH-IMPAIRED INDIVIDUALS", and is hereby incorporated by reference.

The above described methods have been combined in a unique fashion by the present invention to provide an adaptive training method and apparatus for training subjects having abnormal temporal processing abilities to recognize and distinguish short duration acoustic events that are common in speech. More specifically, emphasis has been used to intensify format transitions of stop consonants that are presented to a subject. It is believed that the differential gain of critical acoustic components generates more vigorous neural activity, which leads to better signal differentiation by neural networks involved in speech perception.

The present invention is embodied into a computer program entitled Fast ForWord II by Scientific Learning Corporation. The computer program is provided to an LLI subject via a CD-ROM that is input into a general purpose computer such as that described above with reference to FIG. 1. In addition, a user may log onto a server, via an Internet connection, for example, to upload test results, and to download training parameters for future exercises. Specifics of the present invention will now be described with reference to FIGS. 8–16?.

Figure 8:
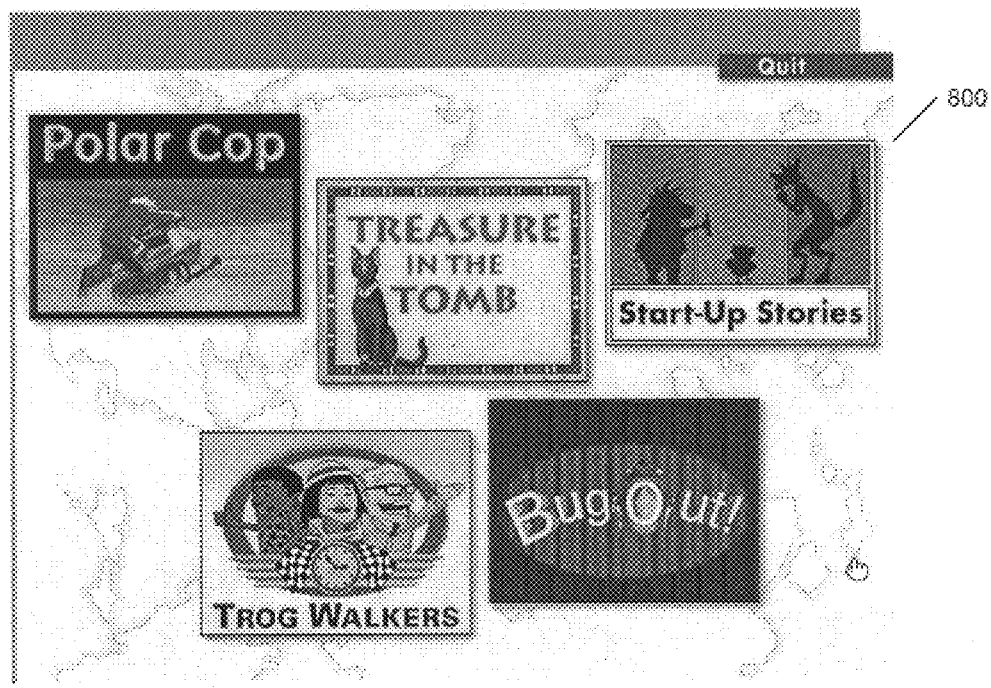
FIG. 8 is a pictorial representation of a game selection screen according to the present invention.

Referring first to FIG. 8, a pictorial representation is shown of a game selection screen 800. The game selection screen 800 is similar to that provided to a subject upon initialization of the computer program according to the present invention. The game selection screen 800 includes the titles of five computer games that provide distinct training exercises for improving language recognition in subjects who abnormally process temporal acoustic events, and for building, or rebuilding the neurological connections necessary to accurately process phonemes at the rates common in speech. The game titles include: 1) Start-Up Stories; 2) Polar Cop; 3) Trog Walkers; 4) Treasure in the Tomb; and 5) Bug-Out!.

When a subject begins execution of the Fast ForWord II computer program, s/he is presented with a screen similar to the screen 800. More specifically, upon initiation of the program, the subject is presented with a screen that lists the subjects that are currently being trained by the program. The subject, or instructor, then selects his/her name from the list. Once the subject has selected his/her name, a screen similar to 800 appears, typically listing the five programs, according to a training schedule that is dictated by the program, or is modified by an instructor. The order of the games that is presented in the screen 800 may vary from day to day, depending on which games the subject has previously played. In addition, after a subject has completed play of a particular game, that game may be shown "grayed out", indicating that it may not be selected again that day unless all other scheduled exercises have already been played. The subject then selects to play one of the games listed.

In one embodiment, a training schedule is provided by a certified Speech and Language Professional (SLP), and the SLP oversees each training session according to the schedule. An exemplary schedule requires a subject to cycle through the games for an hour and forty minutes, five days per week, for approximately six weeks.

In an alternative embodiment, the game schedule is specified by an SLP at a remote server, and the daily parameters of the schedule are downloaded to the subject's computer, either daily or weekly. The schedule can be optimized over the course of the training program according to the performance or skill of the subject. It can also be used to help manage time in each game so that all of the games are completed in about the same time at the end of the training program. This can be accomplished by an automated computer algorithm that adjusts the time allotted for each training exercise. This algorithm is individually adaptive and can adjust the times for each exercise on an individual subject basis using performance and estimates of time to complete the entire training sequence. This embodiment allows a subject to obtain the benefits of the Fast ForWord II program, and the oversight of a certified SLP, regardless of his/her geographic location. One skilled in the art will appreciate that the training schedule could either be provided in a window on the subject's computer, or could actually control the game selection screen to prompt the user only for those games required on a particular day.

Once a subject selects a particular game, s/he is taken into that particular game's module. Alternatively, once the subject selects his/her name from the list, the particular games may be presented, in a predefined order, without requiring the subject to first select the game.

The present application provides a detailed description of the game "Start-Up Stories". The other games shown in FIG. 8 are described in co-pending U.S. Patent Applications: (Polar Copy); (Trog Walkers); (Treasure in the Tomb); and (Bug Out!), which are hereby incorporated by reference.

Start-Up Stories is a game that adaptively trains subjects to improve their ability to parse grammatical constructs, exercises their verbal serial memory, improves their ability to follow complex story lines, and aids in developing listening comprehension. As in the other games mentioned above, Start-Up Stories utilizes acoustic processing to enhance a subject's ability to accurately distinguish between similar sounding phonemes, but the processing is applied to command sentences rather than to individual phonemes. More specifically, Start-Up Stories presents 3 stories to a subject: Chicken Licken, The Big Bad Pigs, and Little Red and the Wolf. Each story consists of four installments, with each installment provided in the following sequence: 1) Narration; 2) Listening Comprehension (LC); 3) Language Comprehension Builder (LCB); and 4) Block Commander (BC).

The Narration installment auditorily and graphically presents a portion of the story to the subject. The subject's task in this installment is to listen carefully to the narration. S/he will not be able to repeat sections of the story, so s/he must listen carefully the first time. This will be further described below with reference to FIGS. 10–11.

Listening Comprehension asks the subject to perform activities that test his/her comprehension of the just narrated installment. For example, in Chicken Licken, the subject will hear questions such as "Who was sitting in the tree?", and "What did Chicken Licken say was falling?" In one embodiment, 4 questions are asked within Listening Comprehension for each narration installment. This will be further described below with reference to FIGS. 12–13.

Language Comprehension Builder asks the subject to perform activities that test his/her comprehension of individual sentences. This will be further described below with reference to FIGS. 14–16.

Block Commander asks the subject to perform tasks on a computer screen in response to sentence directions. This will be further described below with reference to FIGS. 17–19.

Figure 9:
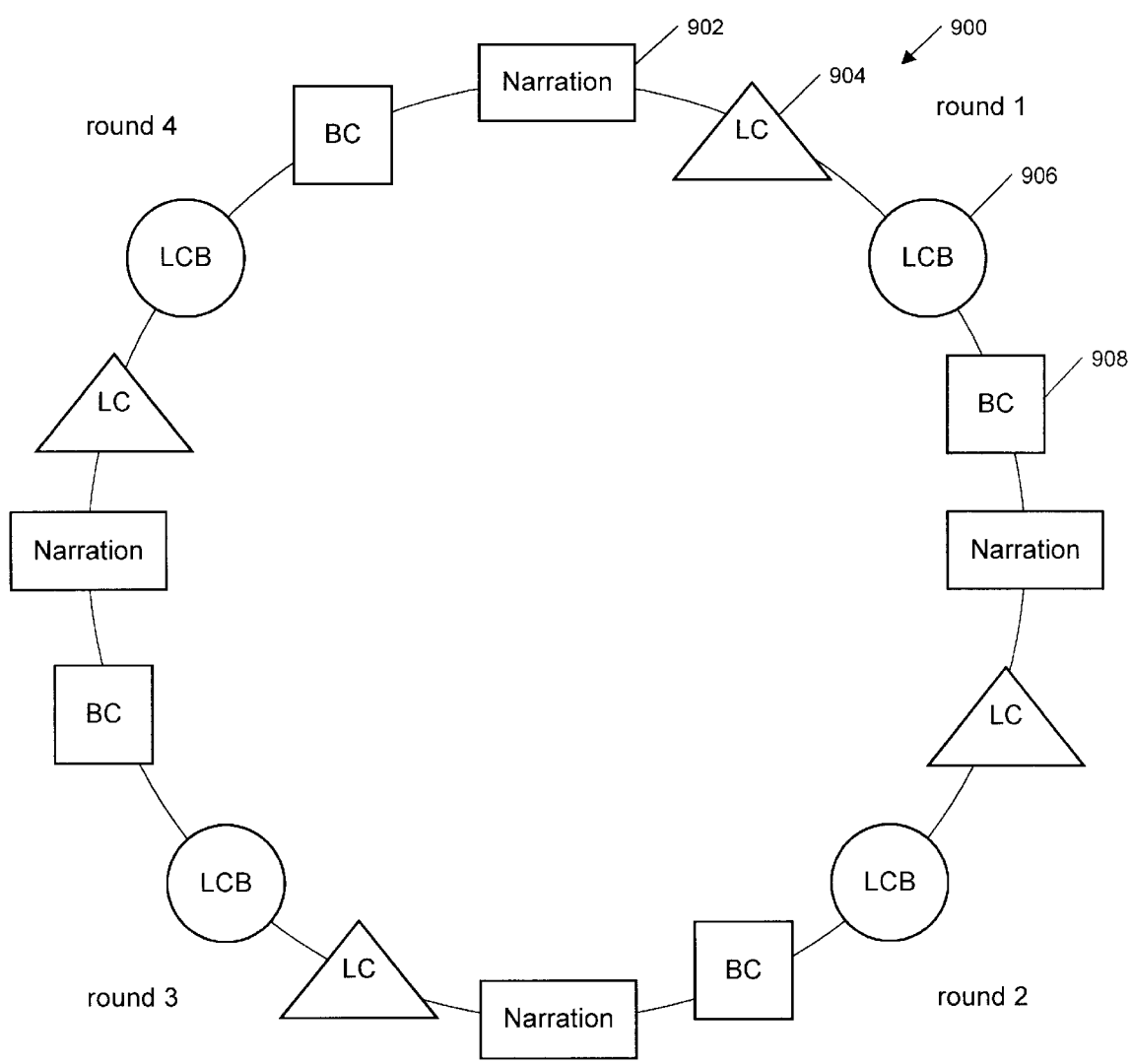
FIG. 9 is a block diagram illustrating the game sequence according to the present invention.
Figure 10:
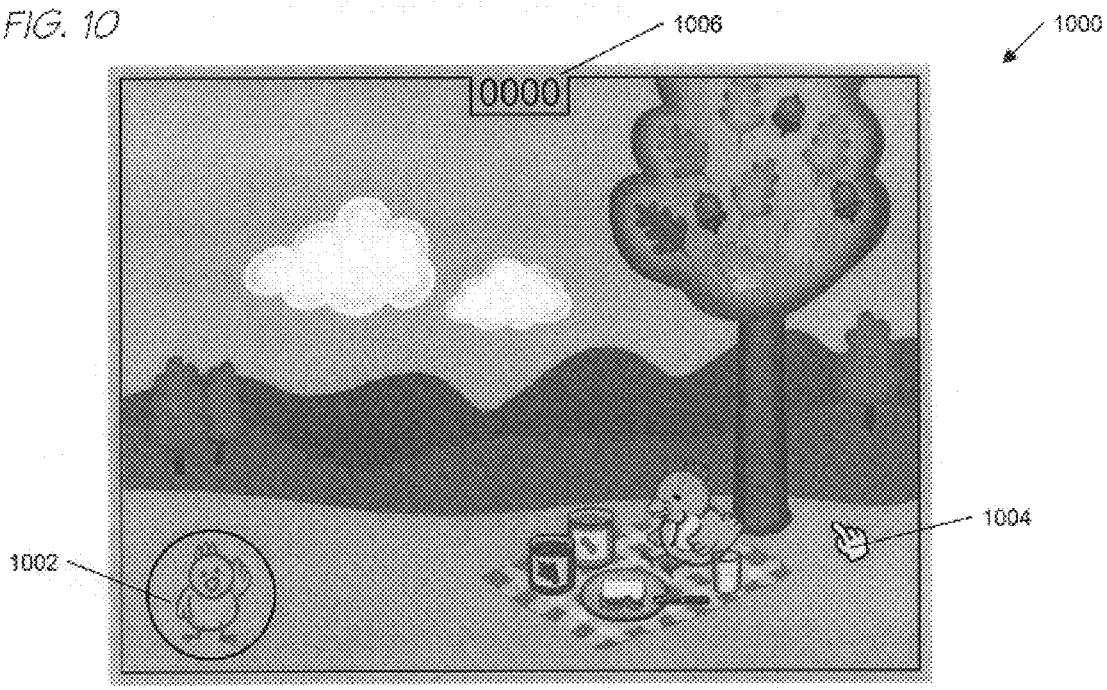
FIG. 10 is a pictorial representation of an initial narration screen portion of the Start-Up Stories game.
Figure 11:
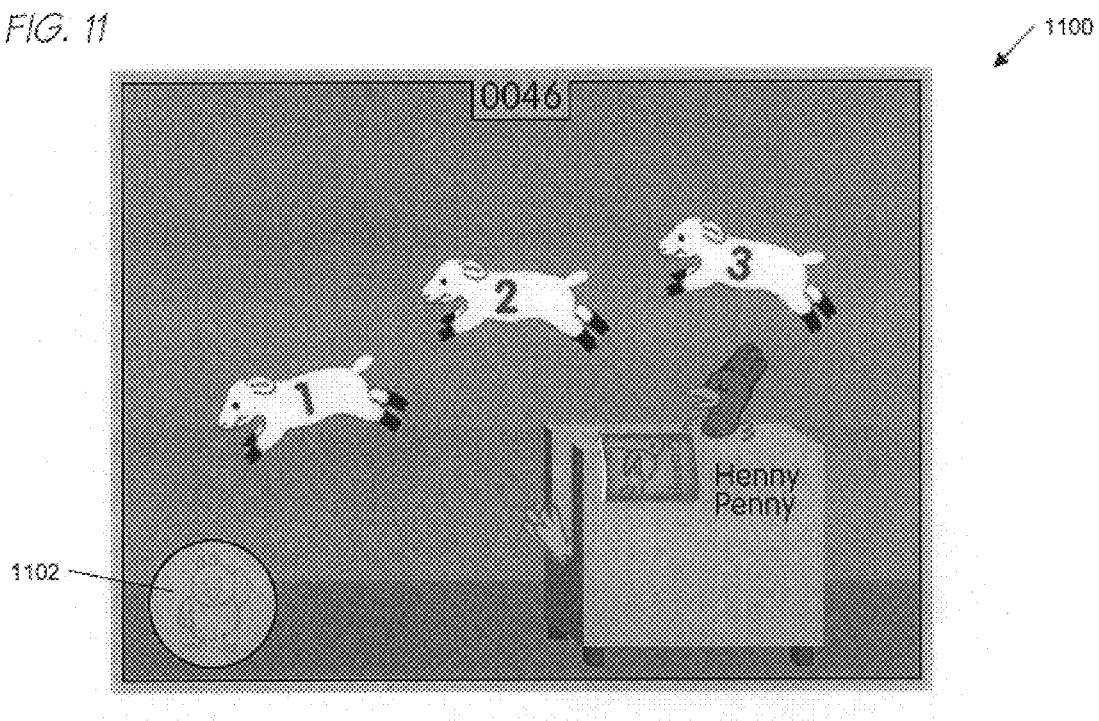
FIG. 11 is a pictorial representation of a subsequent narration screen portion of the Start-Up Stories game.

Referring to FIG. 9, a block diagram 900 is shown that illustrates the progression by a subject through each of the three games provided in Start-Up Stories. Game play begins in round 1 with a Narration installment 902. Once the Narration installment is complete, game play proceeds to a Listening Comprehension installment 904. When complete, game play continues with a Language Comprehension Builder installment 906. When complete, game play continues with a Block Commander installment 908. At this point, round 1 of game play for a particular story is complete. Installments 902–908 are then repeated 3 more times (i.e., rounds 2, 3 and 4), each round presenting another installment of a story, with different questions for each of the installments.

After completion of round 4, a determination is made as to whether the subject has correctly responded to a predetermined percentage trials for that story. If not, then the story repeats, but randomizes the order of the trials within each installment. However, if the subject has correctly responded to the predetermined percentage of trials for that story, the next story within Start-Up Stories is presented.

For each of the stories within Start-Up Stories, speech processing is applied to the consonant (C), or consonant-consonant (CC) portion of words within sentences to assist the subject in distinguishing between similar sounding phonemes or words. In one embodiment, Start-Up Stories provides 3 levels of speech processing for the consonant portion of the words within sentences. Level 1 provides 20 dB of emphasis, and is applied to story 1 (Chicken Licken). Level 2 provides 10 dB of emphasis, and is applied to story 2 (The Big Bad Pigs). Level 3 provides 0 dB of emphasis, and is applied to story 3 (Little Red and the Wolf).

The emphasis uses an algorithm that differentially amplifies and disambiguates faster phonetic elements in speech. "Fast elements" in speech are defined as those that occur in the 3–30 Hz range within an envelope of narrow-band speech channels of a rate changed speech signal. An emphasis algorithm for these fast elements was implemented using two methods: a filter-bank summation method and an overlap-add method based on a short-time Fourier transform. Both of these emphasis algorithms, as well as other speech processing methods are fully described in co-pending U.S. patent application Ser. No. 08/982189, filed Dec. 17, 1997, entitled "METHOD AND APPARATUS FOR TRAINING OF SENSORY AND PERCEPTUAL SYSTEMS IN LLI SUBJECTS".

With the above overview of the Start-Up Stories game, a detailed description of the game screens will now be provided.

Referring to FIG. 16, a screen 1600 is shown of an initial narration installment for the story Chicken Licken. The screen 1600 includes a trial initiation button 1002, a selector hand 1004, and a score 1006. The trial initiation button 1002 is provided in all of the screens, for all of the installments, for all of the stories. It is the button that allows the subject to initiate progression through the game. The trial initiation button 1002 has three states: inactive (shown during presentation of a narration), active (shown at the beginning of each trial), and pressed (shown after the subject selects the button 1002 to begin a new trial).

The subject initiates a trial by moving the selection hand 1004 on top of the trial initiation button 1002, and indicating selection, by pressing a button on a computer mouse, for example.

At the top of the screen 1000, a score indicator 1006 is shown. The score indicator 1006 is also provided in all the screens, across all of the games and all of the stories. The score indicator 1006 provides an indicator to the subject regarding his/her number of correct responses within the Start-Up Stories game.

To begin the narration, the subject selects the trial initiation button 1002. At this point, a first installment of an auditory and visual story is presented to the subject. The narration of the round is read (i.e., played through computer speakers or a headphone). As mentioned above, the processing level used to enhance the narration depends on which story is being told. Thus, as the subject progresses through a story, and correctly responds to a predetermined number of trials, s/he proceeds to a new processing level, and is rewarded with a different story. The narration's that are played in each installment, for each story, are provided below in Appendix A.

Referring to FIG. 1100, a screen 1100 is shown illustrating a subsequent narration screen within round 1 of Chicken Licken. The screen 1100 shows the trial initiation button 1102 in an inactive state because the narration is being presented to the subject. In one embodiment, the narration screens are not static. That is, particular animations are provided within each screen, both to entertain the subject, as well as to provide visual associations with the story. It is believed that such visual associations will assist the subject in becoming a better listener. Once a narration installment of a particular story is presented, Start-Up Stories proceeds immediately to the Listening Comprehension installment of the round.

Figure 12:
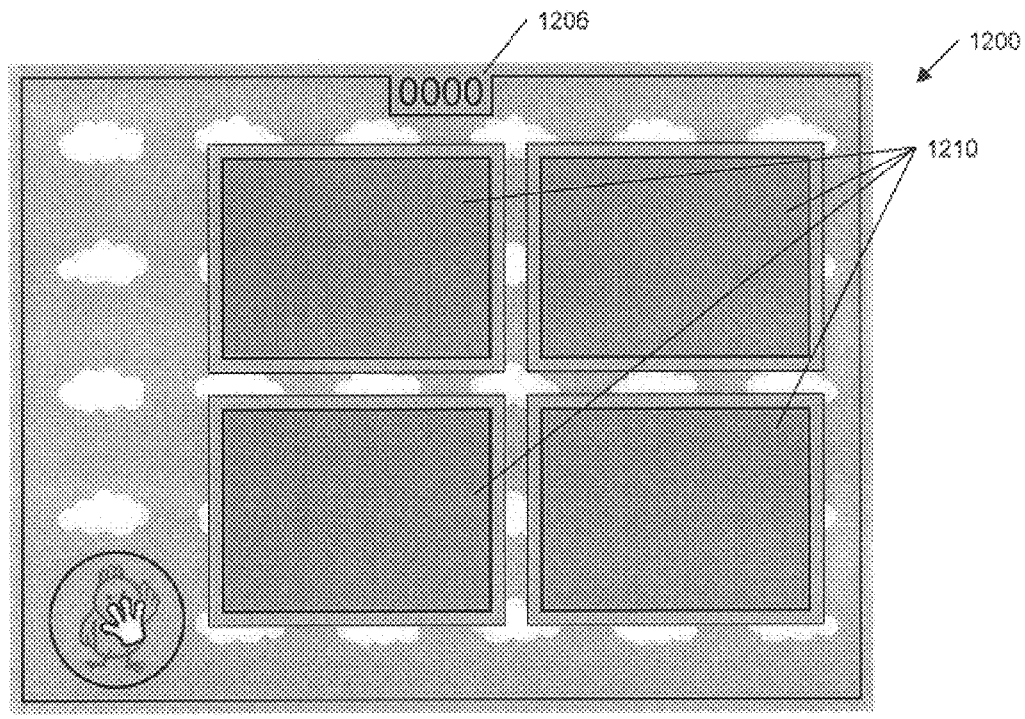
FIG. 12 is a pictorial representation of an initial game screen for the Listening Comprehension portion of the Start-Up Stories game.

Referring to FIG. 12, an initial Listening Comprehension game screen 1200 is shown. The game screen 1200 includes a trial initiation button 1202, a selection hand 1204, and a score indicator 1206, as in the previous screens. The Listening Comprehension game consists of four questions about the narration that has just been presented. The questions are only answerable by subject's that have heard the narration, and were attentive in listening. Each question is accompanied by a set of four cards 1210. Each set of cards 1210 contains one correct answer and three foils. The correct answer and foils are distributed randomly among the cards for each trial.

A subject initiates a trial by selecting the trial initiation button 1202 with the selection hand 1204. At this point, the cards 1210 transition to their "face up" state. A processed sound file unique to the trial is then presented to the subject. When the sound file finishes playing, the cards 1210 become available for selection. A complete list of the questions presented within each round, for each game, is provided in Appendix B. Once a subject selects one of the cards 1210, the game compares it to the correct card. The program provides an auditory "ding" to indicate a correct response, and increases the score indicator 1206 by two points. If the subject incorrectly responds to a trial, by selecting an incorrect card, a "thunk" is played, without any visual feedback.

Figure 13:
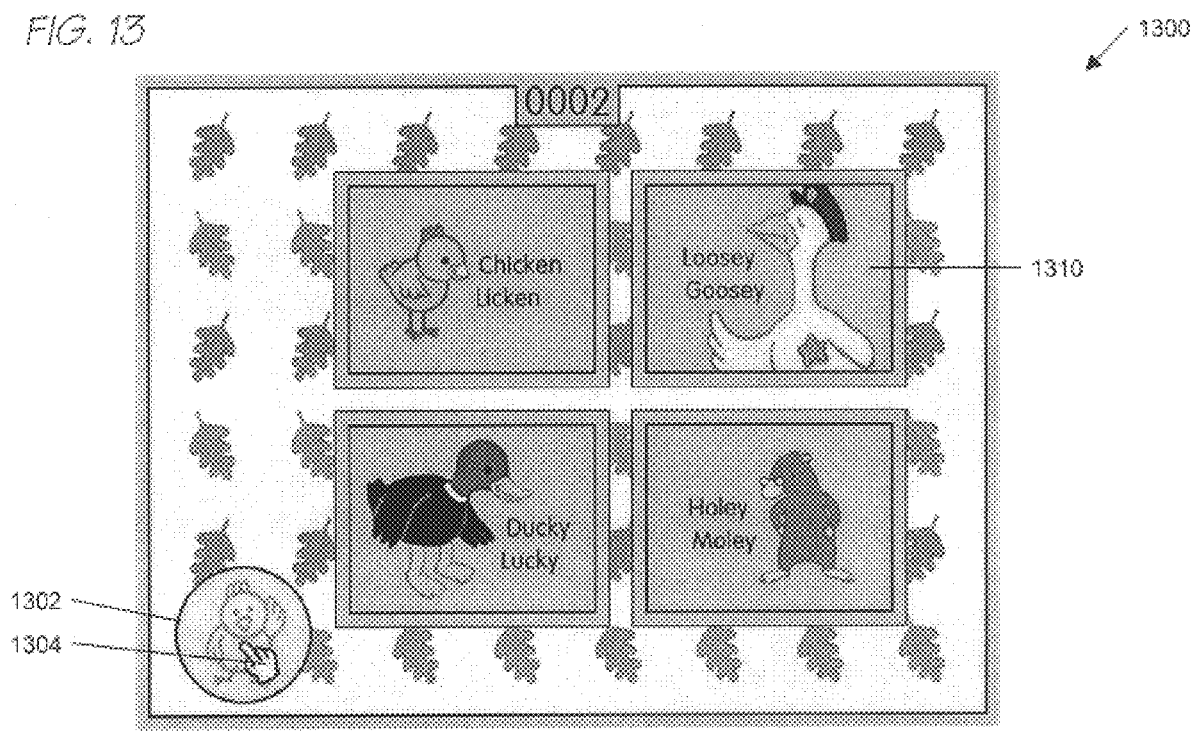
FIG. 13 is a pictorial representation of a subsequent game screen for the Listening Comprehension portion of the Start-Up Stories game.

Referring to FIG. 13, a screen 1300 is shown illustrating a subject initiating a trial, by placing the selection hand 1304 on top of the trial initiation button 1302, and pressing a button on a computer mouse. Cards 1310 appear, one of which is the correct response to the auditorily presented question. The subject responds to the question by selecting one of the cards 1310. After completion of a first trial, the subject must initiate 3 additional trials. When all four trials are completed, the program automatically moves to the Language Comprehension Builder installment.

Figure 14:
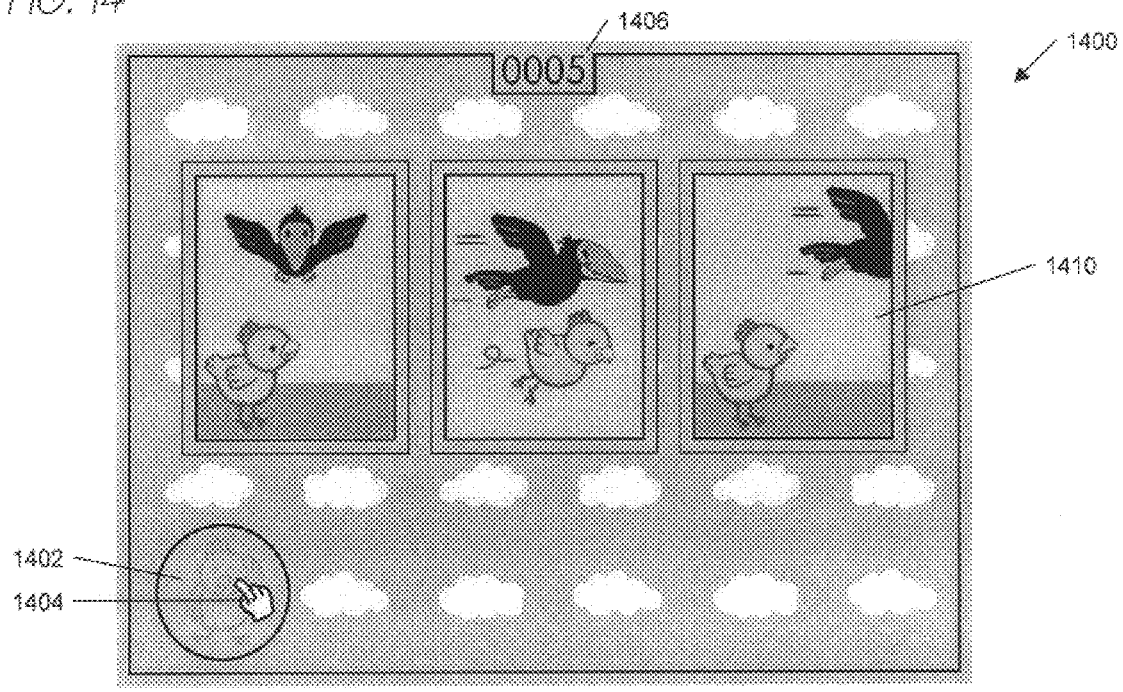
FIG. 14 is a pictorial representation of an initial game screen for the Language Comprehension portion of the Start-Up Stories game.

Referring to FIG. 14, an LCB game screen 1400 is provided. The game screen 1400 includes the trial initiation button 1402, the selection hand 1404 and the score indicator 1406, as in the previously described screens. The LCB installment randomly selects 31 trials from a grammar set (shown in Appendix C). The grammar set consists of questions that are arranged according to skill level, and are grouped as grammar levels 3–8. The grammar levels are represented within each round, with more or less even distribution. More specifically, four trials are presented for each grammar group, in random order. In one pass of a story (4 rounds), a subject will complete 124 trials. In one embodiment, 92 trials are presented from grammar levels 3–6 and 32 trials from levels 7–8. Although Start-Up Stories is configurable, one embodiment requires a subject to correctly respond to 90% of the 92 trials (at levels 3–6) before s/he is allowed to progress to the next processing level, and the next story. If the subject does not meet the 90% threshold, the current story will be repeated, at the current processing level, albeit with randomized order of trials in each installment.

Referring to screen 1400 in each trial within LCB, two to four cards 1410 are presented. The subject initiates the trial by pressing the trial initiation button 1402. A command sentence from one of the grammar levels is then played for the subject in an auditorily processed form, depending on the processing level of the current story. The subject must then select the card 1410 that best represents the sentence that is played. In screen 1400, the sentence played is of the form "The crow is over the chick that is flying".

Figure 15:
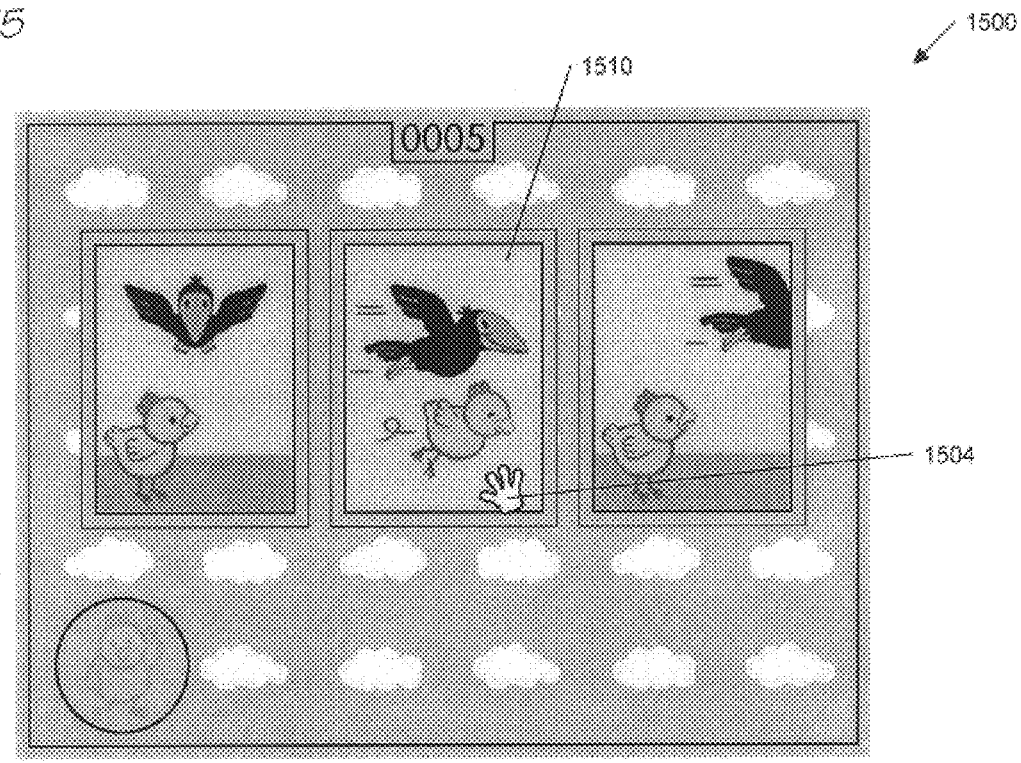
FIG. 15 is a pictorial representation of a game screen showing a subject's correct response to a trial within the game Language Comprehension.

Referring to FIG. 15, a screen 1500 is shown. The screen 1500 illustrates the subject placing the selection hand 1504 over the card 1510 to select the card 1510. If the subject selects the correct card 1510, a "ding" is played. However, if the subject selects the wrong card 1510, a "thunk" is played, and a visual cue is provided indicating the correct response. This is particularly illustrated in FIG. 16, to which attention is now directed.

In FIG. 16, a screen 1600 is shown within the LCB game. The screen 1600 contains two cards 1610, 1611. The subject is shown selecting card 1610 with the selection hand 1604. In screen 1600, card 1610 is an incorrect response. Therefore, the program dims card 1610 to illustrate to the subject that s/he should have selected card 1610. After the subject has initiated and responded to 31 trials within the LCB installment, the game automatically proceeds to the Block Commander installment.

The Block Commander installment consists of twenty trials (five questions for each of four distinct categories). One question from each of the four categories is selected at random, with the category order presented in random order. The categories include: 1) identify (via touch) two objects with two properties each, e.g., touch the green chicken and the blue mole; 2) identify (via touch or removal) two objects with three properties each, e.g., remove the large blue crayon and the large blue hammer; 3) manipulate objects with two properties each, e.g., remove all of the worms, except the red one; and 4) manipulate three objects with at least two properties each, e.g., put the small red house between the brown chicken and the yellow worm. A list of the questions, by category are provided below in Appendix D.

Referring to FIG. 17, a screen 1700 is shown of an initial game screen within the Block Commander installment. A cardframe 1720 is formed to compose a grid (4×4 for example) of cards 1722. The subject initiates a trial by selecting the trial initiation button 1702 with the selection hand 1704. At this point, the cards 1722 change to include objects, although some may remain empty.

Figure 18:
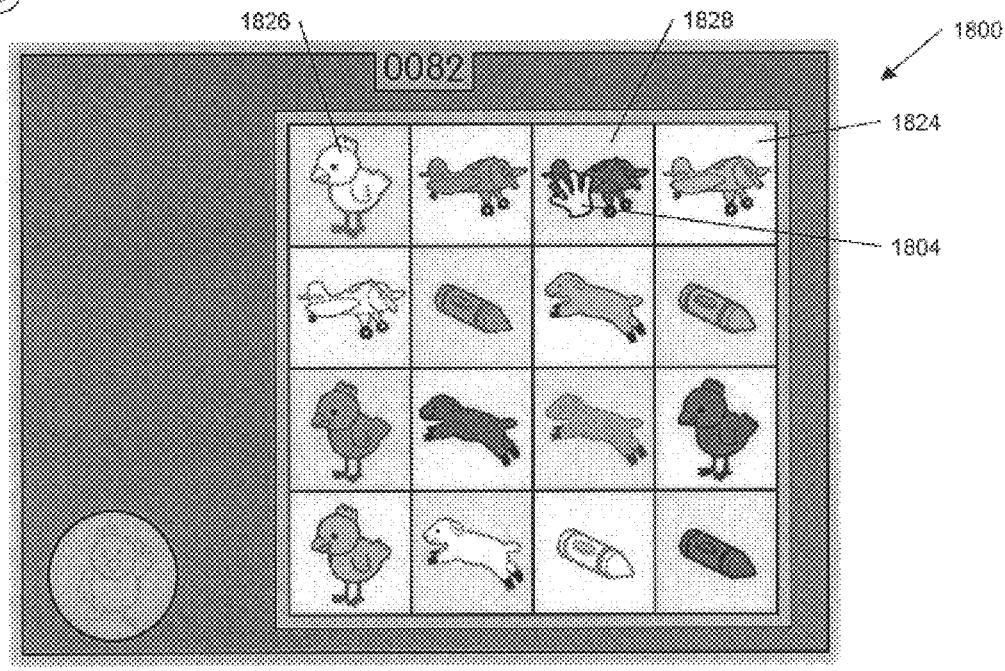
FIG. 18 is a pictorial representation of a game screen showing a subject's correct response to a trial within the game Block Commander.

Referring to FIG. 18, a screen 1800 is shown. The screen 1800 appears as an auditorily processed command sentence is played. In one embodiment, the amount of processing applied to the command sentence is based on the story, or processing level of the round. The screen 1800 includes a plurality of objects 1824 selected from the previous narration or LCB installment, each of which belong to a group of the same objects, but of different color. For example, on the screen 1824, there are four instances of a chick 1826, each of which are presented in a different color (red, blue, yellow, white). The subject is shown selecting a red plane 1828 in response to a command sentence. As mentioned above, the subject will be commanded to either select (via touch) or manipulate (via moving) a number of objects 1824. If the subject correctly selects the commanded objects 1824 s/he will here a "ding". Otherwise, s/he will hear a "thunk". In addition, the program will move the selection hand 1804 to the correct objects 1824, to illustrate to the subject what the correct selection should have been.

Figure 19:
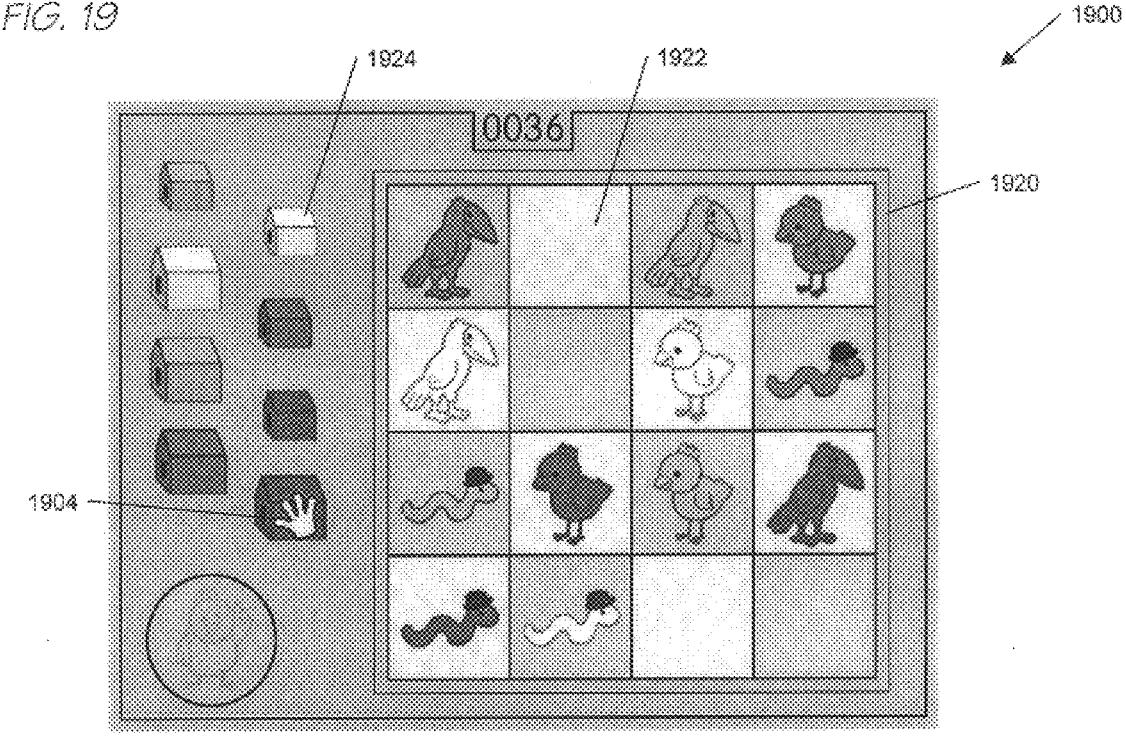
FIG. 19 is a pictorial representation of a game screen illustrating a subject's response within the game Block Commander.

Referring to FIG. 19, a screen 1900 is shown for the Block Commander installment. The cardframe 1920 is shown with a number of empty cards 1922. In addition, a number of objects 1924 are shown outside of the cardframe 1920. In this instance, a command sentence may be of the form "Move all of the large houses, except the blue one". The subject performs the task by placing the selection hand 1904 over the appropriate objects 1924, one at a time, and dragging them onto one of the empty cards 1922. Once all twenty trials have been initiated and responded to, the game proceeds to the next round.

As mentioned above, with reference to FIG. 9, Start-Up Stories includes 4 installments, of 4 rounds, for each story. In addition, each story is associated with a particular processing level. As the subject correctly responds to trials provided in the installments, s/he is allowed to proceed to the next processing level, and thus the next story. However, until the subject obtains a desired threshold of correct responses, s/he will remain at the current processing level, and current story. And, as mentioned above, a threshold of 90% correct responses within four installments of the LCB game is currently required, for the grammar levels 3–6, before the subject is allowed to advance.

The above description provides an overview of how a number of different training methodologies, using auditory processing to enhance phoneme distinctions within speech, are all incorporated into an adaptive game environment that uses a common story to tie them all together. Although the present invention has been described in detail, other embodiments are encompassed by the invention. For example, the methodology of the present invention has been described with reference to a particular game entitled Start-Up Stories It should be appreciated that the stories (such as Chicken Licken) for the game is inconsequential to the methodology used to train a subject in listening comprehension, language comprehension, and serial command processing. While the story line of the game should be engaging and entertaining, other story lines, game scenarios, etc., could be used.

In addition, a particular strategy has been described for adaptively altering command sentence order, and processing level, based on a subject's ability to reach a predetermined threshold. Other performance criteria could be used to modify trial sequencing, without departing from the training methodology encompassed by the present invention.

Furthermore, the trials shown in the Appendices are not exhaustive. Rather, it is believed that they provide significant training for a subject, given particular time constraints on game play imposed by the market. However, additional or alternative stimulus sets are anticipated by the inventors.

Moreover, only 3 speech processing levels have been described for enhancing word recognition. It should be appreciated that additional or alternative speech processing could be used to further enhance a subject's neurological training. Such speech processing could include time expansion, as well as frequency component emphasis, of selected words, and could include varying the Inter-Stimulus-Interval between presented words.

Finally, the Start-Up Stories program has been shown for execution on a personal computer connected to a central server. However, as technology advances, it is envisioned that the program could be executed either by a diskless computer attached to a server, by a handheld processing device, such as a laptop, or eventually by a palmtop device such as a Nintendo GameBoy. As long as the graphical images and auditory prompts can be presented in a timely fashion, and with high quality, the nature of the device used to present the material is irrelevant.

Those skilled in the art should appreciate that they can readily use the disclosed conception and specific embodiments as a basis for designing or modifying other structures for carrying out the same purposes of the present invention without departing from the spirit and scope of the invention as defined by the appended claims.

APPENDIX A

CHICKEN LICKEN

Chapter (Round) One

Chicken Licken was eating lunch one day, when something fell on her head.

"Ow!" she said. "What was that?" She looked up. All she saw was the sky. "The sky is falling!" said Chicken Licken. "I should tell somebody!"

She ran till she saw Squirmy Wormy. "The sky is falling!" said Chicken Licken. "Dig for your life!" said Squirmy Wormy, and wiggled into a hole. Chicken Licken tried to wiggle in after him. But the hole was too small.

She saw Crowy Joey sitting in a tree. "The sky is falling!" said Chicken Licken. "Fly for your life!" said Crowy Joey. He flapped his wings and flew away. Chicken Licken tried to fly, but her wings were too small. She ran all the way to Henny Penny's house.

Chapter (Round) Two

Chicken Licken knocked on the door.

Henny Penny was counting sheep. "Go away," she said. "I'm trying to sleep." Chicken Licken knocked again.

"Come back later," shouted Henny Penny. "I'm laying an egg." Chicken Licken knocked again.

"I'm not buying anything!" shouted Henny Penny. "I'm not selling anything!" shouted Chicken Licken. "The sky is falling!"

Henny Penny jumped up so fast she almost knocked over the fish bowl. "Call 9-1-1!" she cried.

She ran to her desk and picked up the telephone.

Chapter (Round) Three

Henny Penny dialed 9-1-1.

Ducky Lucky answered. "What's the problem?" he asked. "Chicken Licken said the sky is falling!" shouted Henny Penny. "Stay calm, Ma'am," said Ducky Lucky. He punched his assistant, Holey Moley, who was tickling an ant. "Take notes," he said. "Any injuries, Ms. Penny?"

"Any injuries?" asked Henny Penny. "My head hurts," said Chicken Licken. "Her head hurts," said Henny Penny. "Her head hurts," said Ducky Lucky. 'Her head hurts,' Holey Moley wrote in his notebook. "What's your address?" said Ducky Lucky. "One Egg Lane," said Henny Penny. "One Egg Lane," said Ducky Lucky. 'One Egg ane,' wrote Holey Moley.

Ducky Lucky called police headquarters. Officer Loosey Goosey answered. "Goosey here."

"This is Ducky Lucky at 911 Dispatch. Chicken Licken was hit by falling sky near the home of Henny Penny, One Egg Lane. With head injuries."

"I'll get right on it," said Officer Goosey.

Chapter (Round) Four

Officer Goosey called his deputies together.

"Listen up!" he said. "Ducky Lucky reports that Henny Penny reports that Chicken Licken reports the sky is falling. We have injuries. Take extreme care."

An ambulance was rushed to One Egg Lane. Officer Gsoosey followed in his police car with lights flashing. More police cars followed. Egg Lane was blocked off in all directions.

Chicken Licken was rushed to the hospital. Dr. Foxy Loxy took x-rays and performed tests. Henny Penny sat in the waiting room, counting fish in the fish tank to pass the time. She heard the news on the radio.

"Chicken Licken and Henny Penny filed a false report that the sky was falling. Officer Goosey, who found only a small acorn, says charges may be brought against Ms. Licken and Ms. Penny. More news at eleven."

Dr. Loxy came into the waiting room and gave Henny a hug. "Good news," she said. "Chicken Licken is going to be just fine."

Henny kicked the doctor and stomped out the door. "Not when I get through with her!" she said.

THE BIG BAD PIGS

Introduction by the wolf

This is the story of three pigs. I'm the wolf in the story. I'm the good one. The three pigs are big and bad.

I don't hate pigs. Most pigs are cool. I don't hunt them—or eat them. I'm a vegetarian.

So they should have been nice, right? Wrong.

It happened like this.

Chapter (Round) One

There were three pigs: Pinky Pig, her sister Paddle Pig and her brother Punk Pig. They came to build a house next door. That's cool. I like neighbors. I just don't like noise.

So one day I was eating peas and listening to music. But I couldn't hear it. The pigs were next door yelling at each other about what kind of house to build.

Punk Pig was too cool to work. "Let's use straw, sisters," he said. "We'll be done by noon."

"Straw, my curly tail!" said Paddle Pig. "If it rains we'll drown. Let's use sticks. They float."

"It's not a boat, you idiot!" shouted Pinky Pig. "We need a house that won't blow over. We'll use bricks."

"No, straw!" "Sticks, sticks!" "Bricks, I tell you!" It was driving me crazy. I went over there.

"I'm your neighbor-the wolf," I said. "I don't want to interfere, but would you please decide?"

"Who asked you, Wolf?" they said. "Go home!"

Nice neighbors. Anyway, they decided. On three houses.

Chapter (Round) Two

Punk Pig made a straw house. He threw it together and tied it with a rope. "Finished!" he said to the other pigs. Then he rolled in the mud.

Paddle Pig made a stick house. She hammered all day—hammered her hand ("OW!") and her foot ("YOW!"). Finally she got it built. Then she paddled her boat around the pond.

Pinky Pig made a brick house. She worked all day and all night. She dropped some bricks and fell off the ladder. She made so much noise, even the sheep couldn't sleep (they tried counting pigs).

But in the morning Pinky Pig was finished. And very proud of herself. "I have the best house of all," she said.

Punk Pig thought he had the best house. Paddle Pig thought she had the best house.

The pigs started yelling again. It was driving me crazy. I went over there.

Chapter (Round) Three

"Excuse me, but all the houses are nice," I said.

"Oh, it's you," said Paddle Pig. "Since you're so interested in our business, try and blow that straw house down!"

"Yes, blow it down," said Pinky Pig. "Go ahead and try," said Punk Pig.

I wanted to be a good neighbor. So I huffed. I puffed. I blew. The straw house went down—whoosh!

Punk Pig said, "Nice going." And he slugged me. Paddle Pig said, "Nice blowing." And she hugged me.

(What had I gotten myself into?)

"That stick house is no better," said Punk Pig. "Blow it down, Wolf."

"Go for it!" said Pinky Pig. "Go ahead and try," said Paddle Pig.

"Well, okay," I said. "But no slugging. And no hugging."

I huffed again. I puffed again. And blew the stick house right to the ground—clatter—thunk!

"My house is a zero!" said Paddle Pig. And she kicked me. "You're my hero!" said Pinky Pig. And she licked me.

She LICKED me!

I'm a patient guy, but that was too much. I'm Wolf, see? I don't like being licked. "I ought to blow down your house, too, Pinky Pig."

Chapter (Round) Four

The three pigs ran inside the brick house and locked the door.

Pinky Pig shouted, "Don't threaten me, Wolf! You'll never blow this house down."

"We'll see about that," I said. I huffed—I puffed—I blew. Nothing happened.

I huffed again—and puffed again—and BLEW as HARD as I could.

The house never moved.

Okay. So it was brick.

It could have been a mess after that. But the sheep sisters from next door ate the straw. The beaver from down the street took the sticks. And the pigs stayed together in the brick house.

They didn't argue after that, so the neighborhood was quiet again. Of course they hate me. They call me a home wrecker. They throw things at me from their window. Like tomatoes and eggs.

But that's cool. I'm a patient wolf. And like I said . . . I'm a vegetarian.

LITTLE RED AND THE WOLF

Chapter (Round) One

Once upon a time, there was a little girl who lived in the suburbs. She wore a red cape and hood her Granny had made, so everyone called her Little Red.

But Little Red hated that cape, and one day she threw it in the trash. Her mother came into her room with a basket of treaties.

"Granny has a cold," she said. "Be a dear and take this basket to her. And wear that cape she made for you."

Little Red was furious.

"I hate that cape!" she said. And I won't go over there and watch Granny sneeze! I want to watch TV."

Her mother put her foot down. "You will go," she said. "Or no TV for a very long time."

Little Red grumbled things no one should hear. She pulled the red cape out of the trash and put it on.

"It could use a little ironing," said her mother. "But never mind. Go straight to Granny's and don't talk to strangers."

Little Red grumbled all the way out the door.

Chapter (Round) Two

Granny lived a few blocks away. But Little Red took the long way, through the woods.

The woods were cool. There were birds chirping in the trees. Fish jumping in the stream. And deer munching on leaves. It was all very scenic.

All except for the scraggilywolf leaning against a tree.

"Hey there," said the wolf. "What's in the basket?"

"I can't talk to you," said Little Red. "And what are you doing in the suburbs?"

"I'm part of the story," said the wolf. "Don't you read?"

"Don't cross me," said Little Red. "I'm in a bad mood."

"And I'm starving," said the wolf. "So you're taking the basket to Granny's house, right?" "Right," said Little Red. "I get to watch her sneeze."

"I could help you out," said the wolf. "If you help me."

"How's that?" asked Little Red.

The wolf whispered his plan in the little girl's ear.

"You're very clever," smiled Little Red. "I'm a wolf," smiled the wolf.

Chapter (Round) Three

Granny was in bed, sneezing, when she heard a knock at the door. She didn't look so good. Her hair was messy. Her house was dusty. And the goldfish was hungry. But after all, Granny was sick.

"Who is it?" she said. "It's Little Red," said a voice.

"Come in, child," said Granny.

Little Red came inside, carrying the basket. The hood was pulled down clear to her nose.

"How lovely to see you," said Granny.

"And what a nice basket of treaties you brought."

"It's from my dear mother," said Little Red. "It's lovely to see you, too."

"My, you've gotten tall," said Granny. "Well," said Little Red. "I'm a growing girl."

"And I can hardly see you. Take off the hood, dear." "Oh, I love it too much to take it off," said Little Red.

"And your nose . . . " said Granny. "It's very—long."

Little Red began to cry. "Do you think it's ugly, Granny?"

"Oh, no, dear, it's a lovely nose," said Granny.

She lied. It was the ugliest little girl nose she had ever seen.

Chapter (Round) Four

"Let's dig into that basket," she said, changing the subject. Little Red seemed to like that idea—a lot.

They sat at the kitchen table and dug in.

There was vegetable soup, fresh hot bread and chocolate chip cookies. They ate everything.

Then they both felt better. But Granny was still sick, and—'Ah ah ah—CHOO!'She sneezed.

Little Red's hood blew right off her head.

"You're not Little Red," cried Granny. "You're a dog!"

"Actually—I'm a wolf," said the wolf. "Red went to a friend's house to watch TV."

Granny seemed fine with that.

"I never did care for that child," she said. But you are welcome to stay."

"Don't mind if I do," said the wolf.

"It's not safe in the suburbs for a guy like me."

The wolf moved into Granny's spare room. He dusted and cleaned and kept the goldfish fed. Granny and the wolf became great friends.

When visitors came, he wore the cape and hood, and Granny called him 'Little Red.' So no one ever knew there was a wolf in the house.

They did think, though, that Little Red was the ugliest little girl they had ever seen.

APPENDIX B

Chicken Licken Listening Comprehension Questions

Card (a) is always the correct answer. Naming convention for cards: CL1 LC1a, CL1 LC1b, etc Naming convention for casts: CL1_LCcards.cst, CL2_LCcards.cst, etc Round One Questions CL1 LC1 What was Chicken Licken doing when something fell on her head?
- a. eating
- b. running
- c. reading
- d. falling CL1 LC2 What did Chicken Licken say was falling?
- a. sky
- b. book
- c. acorn
- d. sandwich CL1 LC3 Who was sitting in the tree?
- a. Crowy Joey
- b. Henny Penny
- c. Chicken Licken
- d. Squirmy Wormy CL1 LC4 Whose house did Chicken Licken visit?
- a. Henny Penny
- b. Crowy Joey
- c. Ducky Lucky
- d. Squirmy Wormy Round Two Questions CL2 LC1 On what did Chicken Licken knock?
- a. door
- b. fish bowl
- c. magazine
- d. lamp CL2 LC2 What was Henny Penny counting?
- a. sheep
- b. telephones
- c. eggs
- d. fish CL2 LC3 What did Henny Penny almost knock over?
- a. fish bowl
- b. telephone
- c. magazine
- d. pizza CL2 LC4 What did Henny Penny pick up from her desk?
- a. telephone
- b. fish bowl
- c. magazine
- d. pizza Round Three Questions CL3 LC1 Who answered the phone when Henny Penny called?
- a. Ducky Lucky
- b. Chicken Licken
- c. Loosey Goosey
- d. Holey Moley CL3 LC2 Whom was Holey Moley tickling?
- a. an ant
- b. Chicken Licken
- c. Ducky Lucky
- d. Henny Penny CL3 LC3 What part of Chicken Licken hurt?
- a. head
- b. eye
- c. foot
- d. heart CL3 LC4 Who called police headquarters?
- a. Ducky Lucky
- b. Chicken Licken
- c. Loosey Goosey
- d. Henny Penny Round Four Questions CL4 LC1 What was rushed to One Egg Lane?
- a. ambulance
- b. radio
- c. acorn
- d. police car CL4 LC2 Who was rushed to the hospital?
- a. Chicken Licken
- b. Ducky Lucky
- c. Loosey Goosey
- d. Foxy Loxy CL4 LC3 What did Henny Penny count?
- a. fish
- b. radios
- c. acorns
- d. sheep CL4 LC4 What did Officer Loosey Goosey find?
- a. acorn
- b. radio
- c. sandwich
- d. sheep

The Big Bad Pigs Listening Comprehension Questions

Card (a) is always the correct answer. Naming convention for cards: BP1 LC1a, BP1 LC1b, etc Naming convention for casts: BP1_LCcards.cst, BP2_LCcards.cst, etc Round One Questions
BP1 LC1 What was the wolf eating?
a. peas
b. a sandwich
c. pork chops
d. a chicken dinner
BP1 LC2 Who was too cool to work?
a. Punk Pig
b. Paddle Pig
c. Pinky Pig
d. Wolf
BP1 LC3 What did Pinky Pig want to use to build her house?
a. Bricks
b. Sticks
c. Straw
d. Boards
BP1 LC4 How many houses did the pigs decide to build?
a. Three
b. Four
c. Two
d. One
Round Two Questions
BP2 LC1 Who finished building their house first?
a. Punk Pig
b. Paddle Pig
c. Pinky Pig
d. Wolf
BP2 LC2 Of what was Paddle Pig's house made?
a. Sticks
b. Bricks
c. Straw
d. Rocks
BP2 LC3 Who used a hammer to build their house?
a Paddle Pig
b. Punk Pig
c. Pinky Pig
d. Wolf
BP2 LC4 What did Pinky Pig drop?
a. bricks
b. hammer
c. sticks
d. straw
Round Three Questions
BP3 LC Who said "try and blow down the straw house"?
a. Paddle Pig
b. Punk Pig
c. Pinky Pig
d. Wolf
BP3 LC2 Who said "blow down the stick house"?
a. Punk Pig
b. Paddle Pig
c. Pinky Pig
d. Wolf
BP3 LC3 What did Paddle Pig first do to the wolf?
a. hugged her
b. kicked her
c. licked her
d. slugged her BP3 LC4 What did Pinky Pig do to the wolf?
a. licked her
b. kicked her
c. hugged her
d. slugged her
Round Four Questions
BP4 LC1 The three pigs ran inside a house. What was used to make the house?
a. bricks
b. sticks
c. straw
d. rocks
BP4 LC2 Who ate the straw?
a. Sheep sisters
b. Beaver
c. Wolf
d. Pigs
BP4 LC3 Who took the sticks?
a. Beaver
b. Sheep sisters
c. Wolf
d. Pigs
BP4 LC4 What did the pigs throw from their window?
a. eggs
b. bricks
c. sticks
d. straw Little Red and The Wolf Listening Comprehension Questions Card (a) is always the correct answer. Naming convention for cards: LR1 LC1*a*, LR1 LC1*b*, etc Naming convention for casts: LR1_LCcards.cst, LR2_LCcards.cst, etc
Round One Questions
LR1 LC1 Where did Little Red live?
a. suburbs
b. woods
c. city
d. country
LR1 LC2 Where did Little Red put her cape?
a. trash
b. closet
c. on her bed
d. on a chair
LR1 LC3 What did Little Red take to her Granny?
a. basket
b. a cape
c. a TV
d. an iron
LR1 LC4 What did Little Red want to do?
a. watch TV
b. go to granny's house
c. go to bed
d. read a book
Round Two Questions
LR2 LC1 Who was jumping?
a. fish
b. deer
c. birds d. Wolf
LR2 LC2 Who was leaning against a tree?
a. Wolf
b. deer
c. bird
d. Little Red
LR2 LC3 Who offered to help Little Red?
a. Wolf
b. deer
c. bird
d. fish
LR2 LC4 Who was munching on leaves?
a. deer
b. wolf
c. bird
d. fish
Round Three Questions
LR3 LC1 Who was hungry?
a. goldfish
b. Granny
c. Little Red
d. Wolf
LR3 LC2 Who's hair was Messy?
a. Granny
b. Little Red
c. deer
d. Wolf
LR3 LC3 Who was sick?
a. Granny
b. Little Red
c. deer
d. Wolf
LR3 LC4 Where was Granny?
a. in bed
b. on the couch
c. in a chair
d. standing by the door
Round Four Questions
LR4 LC1 Where did they sit while eating the treats?
a. kitchen table
b. on the bed
c. on the couch
d. on the floor
LR4 LC2 Which item was not in the basket?
a. apple
b. soup
c. rolls
d. cookies
LR4 LC3 Who became great friends with Granny?
a. Wolf
b. Little Red
c. deer
d. goldfish
LR4 LC4 Who fed the goldfish?
a. Wolf
b. Granny
c. Little Red
d. deer

APPENDIX C

CHICKEN LICKEN
Chapter (Round) One Questions
3/7
1. The chicken sees the clouds in the sky.
a. The chicken sees the clouds in the sky.
b. The chicken sees the cloud in the sky.
2. Chicken Licken finds the worm on the ground.
a. Chicken Licken finds the worm on the ground.
b. Chicken Licken finds the worms on the ground.
3. The chicken sees the worm wiggling into the hole.
a. The chicken sees the worm wiggling into the hole.
b. The chicken sees the worms wiggling into the hole.
4. The crow flaps his wings.
a. The crow flaps his wings.
b. The crow flaps his wing.
3/13
1. The chicken that is little is not eating.
a. The chicken that is little is not eating.
b. The chicken that is little is eating.
c. The chicken that is not little is not eating.
d. The chicken that is not little is eating.
2. The worm that is not in the hole is wearing a hat.
a. The worm that is not in the hole is wearing a hat.
b. The worm that is not in the hole is not wearing a hat.
c. The worm that is in the hole is wearing a hat.
d. The worm that is in the hole is not wearing a hat.
3. The crow that is not happy is flying.
a. The crow that is not happy is flying.
b. The crow that is happy is flying.
c. The crow that is not happy is not flying.
d. The crow that is not happy is flying.
4. The chicken that is running is not happy.
a. The chicken that is running is not happy.
b. The chicken that is running is happy.
c. The chicken that is not running is happy.
d. The chicken that is not running is not happy.
4/20
1. The chicken is eating lunch.
a. The chicken is eating lunch.
b. The chicken ate lunch.
c. The chicken will eat lunch.
2. The worm is wiggling into a hole.
a. The worm is wiggling into a hole.
b. The worm wiggled into a hole.
c. The worm will wiggle into a hole.
3. The crow is flying away.
a. The crow is flying away.
b. The crow flew away.
c. The crow will fly away.
4. The chicken is jumping.
a. The chicken is jumping.
b. The chicken jumped.
c. The chicken will jump.
5/23
1. The hole is dug for the worm.
a. The hole is dug for the worm.
b. The hole is dug with the worm.
c. The hole is dug by the worm.

2. The sandwich is made for the chicken.
a. The sandwich is made for the chicken.
b. The sandwich is made with the chicken.
c. The sandwich is made by the chicken.
3. The birdhouse is made for the crow.
a. The birdhouse is made for the crow.
b. The birdhouse is made by the crow.
c. The birdhouse is made with the crow.
4. The tablecloth is laid down the chicken.
a. The tablecloth laid down for the chicken.
b. The tablecloth is laid down with the chicken.
c. The tablecloth is laid down by the chicken.
6/29
1. The chicken is digging with the worm.
a. The chicken is digging with the worm.
b. The chicken is digging to the worm.
c. The chicken is digging from the worm.
2. The crow is flying with the chicken.
a. The crow is flying with the chicken.
b. The crow is flying to the chicken.
c. The crow is flying from the chicken.
3. The chicken is running with her lunch.
a. The chicken is running with her lunch.
b. The chicken is running to her lunch.
c. The chicken is running from her lunch.
4. The birdhouse is falling with the branch.
a. The birdhouse is falling with the branch.
b. The birdhouse is falling to the branch.
c. The birdhouse is falling from the branch.
6/31
1. The chicken chasing the worm that is crawling is running.
  a. The chicken chasing the worm that is crawling is running.
  b. The chicken chasing the worm that is crawling is crawling.
  c. The chicken chasing the worm that is running is crawling.
  d. The chicken chasing the worm that is running is running.
2. The worm digging the dirt that is brown is red.
a. The worm digging the dirt that is brown is red.
b. The worm digging the dirt that is brown is brown.
c. The worm digging the dirt that is red is brown.
d. The worm digging the dirt that is red is red.
3. The crow sitting in the tree that is big is little.
a. The crow sitting in the tree that is big is little.
b. The crow sitting in the tree that is big is big.
c. The crow sitting in the tree that is little is big.
d. The crow sitting in the tree that is little is little.
4. The chicken hugging the crow that is happy is scared.
a. The chicken hugging the crow that is happy is scared.
b. The chicken hugging the crow that is happy is happy.
c. The chicken hugging the crow that is scared is happy.
d. The chicken hugging the crow that is scared is scared.
7/34
1. What is in the sky? (sandwich)
a. What is in the sky? (sandwich)
b. Who is in the sky? (Chicken Licken falling . . . ?)
c. Is nothing in the sky?
2. Who is digging a hole? (Chicken Licken)
a. Who is digging a hole? (Chicken Licken)
b. What is digging a hole? (shovel)
3. Is nothing digging a hole?
3. Who is in the hole? (Squirmy Wormy)
a. Who is in the hole? (Squirmy Wormy)
b.What is in the hole? (Chicken Licken's sandwich . . . ?)
c. Is nothing in the hole?
4. What is on the branch? (Chicken Licken's sandwich . . . ?)
  a. What is on the branch? (Chicken Licken's sandwich . . . ?)
  b. Who is on the branch? (Crowy Joey)
  c. Is nothing on the branch?
8/38
1. It's the worm that the chicken follows.
a. It's the worm that the chicken follows.
b. It's the chicken that the worm follows.
c. It's the crow that the worm follows.
d. It's the crow that the chicken follows.
2. It's the dirt that the leaf covers.
a. It's the dirt that the leaf covers.
b. It's the leaf that the dirt covers.
c. It's the worm that the dirt covers.
d. It's the worm that the leaf covers.
3. It's the crow that the chicken hugs.
a. It's the crow that the chicken hugs.
b. It's the chicken that the crow hugs.
c. It's the worm that the crow hugs.
d. It's the worm that the chicken hugs.
4. It's the chicken that crow leaves.
a. It's the chicken that the crow leaves.
b. It's the crow that the chicken leaves.
c. It's the worm that the chicken leaves.
d. It's the worm that the row leaves.
Round Two Questions
4/18
1. The nest has none. (eggs) (belongs to grammar group 3/8—was Q2)
a. The nest has none.
b. The nest has one.
c. The nest has some.
d. The nest has many.
2. The egg has some. (spots)
a. The egg has some. (spots)
b. The egg has many.
c. The egg has none.
d. The egg has one.
3. Henny Penny counts some. (sheep)
a. Henny Penny counts some. (sheep)
b. Henny Penny counts none.
c. Henny Penny counts one.
d. Henny Penny counts many.
4. The telephone has none. (numbers) (belongs to grammar group 3/8—was Q4)
a. The telephone has none. (numbers)
b. The telephone has many.
c. The telephone has one.
d. The telephone has some.

4/19
1. The sheep leaps.
   a. The sheep leaps.
   b. The sheep leap.
2. The fish fly. (belongs to grammar group 8/35—was Q2)
   a. The fish fly.
   b. The fish flies.
3. The sheep sleeps.
   a. The sheep sleeps.
   b. The sheep sleep.
4. The fish cry. (belongs to grammar group 8/35—was Q4)
   a. The fish cry.
   b. The fish cries.

3/8
1. The bowl has none. (fish)
   a. The bowl has none. (fish)
   b. The bowl has many.
   c. The bowl has some.
   d. The bowl has one.
2. Henny Penny's nest has some. (eggs) (belongs to grammar group 4/18—was Q1)
   a. Henny Penny's nest has some. (eggs)
   b. Henny Penny's nest has one.
   c. Henny Penny's nest has many.
   d. Henny Penny's nest has none.
3. The hen counts none. (sheep)
   a. The hen counts none. (sheep)
   b. The hen counts some.
   c. The hen counts one.
   d. The hen counts many.
4. The telephone has some. (numbers) (belongs to grammar group 4/18—was Q4)
   a. The telephone has some. (numbers)
   b. The telephone has one.
   c. The telephone has many.
   d. The telephone has none.

3/15
1. The egg is bigger.
   a. The egg is bigger.
   b. The egg is smaller.
2. The fish is fatter.
   a. The fish is fatter.
   b. The fish is thinner.
3. The sheep leaps higher.
   a. The sheep leaps higher.
   b. The sheep leaps lower.
4. The desk is messier.
   a. The desk is messier.
   b. The desk is cleaner.

6/28
1. Which is the fish's dinner?
   a. Which is the fish's dinner?
   b. Which is the fish dinner?
2. Which is the chicken's sandwich?
   a. Which is the chicken's sandwich?
   b. Which is the chicken sandwich?
3. Which is the baby chicken?
   a. Which is the baby chicken?
   b. Which is the baby's chicken?
4. Which is the giant's egg?
   a. Which is the giant's egg?
   b. Which is the giant egg?

7/33
1. The sheep leaping over the hen is grinning.
   a. The sheep leaping over the hen is grinning.
   b. The hen leaping over the sheep is grinning.
   c. The sheep leaping over the hen is frowning.
   d. The hen leaping over the sheep is frowning.
2. The hen sifting on the egg is white.
   a. The hen sitting on the egg is white.
   b. The egg sitting on the hen is white.
   c. The hen sitting on the egg is brown.
   d. The egg sitting on the hen is brown.
3. The hen hugging the chicken is crying.
   a. The hen hugging the chicken is crying.
   b. The chicken hugging the hen is crying.
   c. The hen hugging the chicken is laughing.
   d. The chicken hugging the hen is laughing.
4. The big fish chasing the little fish is orange.
   a. The big fish chasing the little fish is orange.
   b. The little fish chasing the big fish is orange.
   c. The big fish chasing the little fish is black.
   d. The little fish chasing the big fish is black.

6/27
1. The sheep will jump over Henny Penny.
   a. The sheep will jump over Henny Penny.
   b. The sheep jumped over Henny Penny.
   c. The sheep is jumping over Henny Penny.
2. Henny Penny will lay an egg.
   a. Henny Penny will lay an egg.
   b. Henny Penny is laying an egg.
   c. Henny Penny laid an egg.
3. The egg will fall out of the nest.
   a. The egg will fall out of the nest.
   b. The egg is falling out of the nest.
   c. The egg fell out of the nest.
4. The egg will hatch.
   a. The egg will hatch.
   b. The egg is hatching.
   c. The egg hatched.

8/35
1. The sheep leap.
   a. The sheep leap.
   b. The sheep leaps.
2. The fish swims. (belongs to grammar group 4/19—was Q2)
   a. The fish swims.
   b. The fish swim.
3. The sheep sleep.
   a. The sheep sleep.
   b. The sheep sleeps.
4. The fish jumps. (belongs to grammar group 4/19—was Q4)
   a. The fish jumps.
   b. The fish jump.

Round Three Questions
4/16
1. The ant is being tickled by the mole.
   a. The ant is being tickled by the mole.

b. The mole is being tickled by the ant.
c. The ant is being tickled by the duck.
d. The duck is being tickled by the mole.
2. The duck is being telephoned by the hen.
a. The duck is being telephoned by the hen.
b. The hen is being telephoned by the duck.
c. The duck is being telephoned by the ant.
d. The ant is being telephoned by the hen.
3. The mole is being punched by the duck.
a. The mole is being punched by the duck.
b. The duck is being punched by the mole.
c. The mole is being punched by the ant.
d. The ant is being punched by the duck.
4. The hen is being hugged by the chicken.
a. The hen is being hugged by the chicken.
b. The chicken is being hugged by the hen.
c. The hen is being hugged by the fish.
d. The fish is being hugged by the chicken.

4/21
1. Holey Moley wrote a word.
a. Holey Moley wrote a word.
b. Holey Moley wrote some words.
2. Chicken Licken feeds some fish.
a. Chicken Licken feeds some fish.
b. Chicken Licken feeds a fish.
3. Chicken Licken has a bump.
a. Chicken Licken has a bump.
b. Chicken Licken has some bumps.
4. There are some ants biting Ducky Lucky.
a. There are some ants biting Ducky Lucky.
b. There is an ant biting Ducky Lucky.

5/26
1. She is shouting.
a. She is shouting.
b. He is shouting.
c. They are shouting.
2. He is punching.
a. He is punching.
b. She is punching.
c. They are punching.
3. He is taking notes.
a. He is taking notes.
b. They are taking notes.
c. She is taking notes.
4. They are swimming.
a. They are swimming.
b. She is swimming.
c. He is swimming.

3/9
1. The mole wearing glasses is tickling the ant.
a. The mole wearing glasses is tickling the ant.
b. The ant wearing glasses is tickling the mole.
c. The mole wearing a hat is tickling the ant.
d. The ant wearing a hat is tickling the mole.
2. The hen who is frightened is shouting at the duck.
a. The hen who is frightened is shouting at the duck.
b. The duck who is frightened is shouting at the hen.
c. The hen who is happy is shouting at the duck.
d. The duck who is happy is shouting at the hen.
3. The ant who has spots is biting the mole.
a. The ant who has spots is biting the mole.
b. The mole who has spots is biting the ant.
c. The ant who has stripes is biting the mole.
d. The mole who has stripes is biting the ant.
4. The chicken who is yellow is feeding the fish.
a. The chicken who is yellow is feeding the fish.
b. The fish who is yellow is feeding the chicken.
c. The chicken who is pink is feeding the fish.
d. The fish who is pink is feeding the chicken.

3/11
1. Who is more frightened?
a. Who is more frightened?
b. Who is less frightened?
2. Who is more ticklish?
a. Who is more ticklish?
b. Who is less ticklish?
3. Who is more injured?
a. Who is more injured?
b. Who is less injured?
4. Who is more colorful?
a. Who is more colorful?
b. Who is less colorful?

6/30
1. The duck who is punching the mole who is little is big.
a. The duck who is punching the mole who is little is big.
b. The duck who is punching the mole who is big is little.
c. The duck who is punching the mole who is big is big.
d. The duck who is punching the mole who is little is little.
2. The hen who is hugging the chicken who is sad is happy.
a. The hen who is hugging the chicken who is sad is happy.
b. The hen who is hugging the chicken who is happy is sad.
c. The hen who is hugging the chicken who is happy is happy.
d. The hen who is hugging the chicken who is sad is sad.
3. The ant who is biting the mole who is gray is red.
a. The ant who is biting the mole who is gray is red.
b. The ant who is biting the mole who is red is gray.
c. The ant who is biting the mole who is gray is gray.
d. The ant who is biting the mole who is red is red.
4. The chicken who is watching the sheep that is jumping is sitting.
a. The chicken who is watching the sheep that is jumping is sitting.
b. The chicken who is watching the sheep that is sitting is jumping.
c. The chicken who is watching the sheep that is jumping is jumping.
d. The chicken who is watching the sheep that is sitting is sitting.

8/37
1. The duck is punching the mole that the ant is biting.
a. The duck is punching the mole that the ant is biting.
b. The duck is punching the mole that is biting the ant.
c. The duck is punching the ant that the mole is biting.
d. The duck is punching the ant that is biting the mole.
2. The hen is shouting at the duck that the mole is tickling.

a. The hen is shouting at the duck that the mole is tickling.
b. The hen is shouting at the duck that is tickling the mole.
c. The hen is shouting at the mole that the duck is tickling.
d. The hen is shouting at the mole that is tickling the duck.
3. The mole is kicking the duck that the ant is tickling.
a. The mole is kicking the duck that the ant is tickling.
b. The mole is kicking the duck that is tickling the ant.
c. The mole is kicking the ant that the duck is tickling.
d. The mole is kicking the ant that is tickling the duck.
4. The sheep leaps over the fish that the chicken is catching.
a. The sheep leaps over the fish that the chicken is catching.
b. The sheep leaps over the fish that is catching the chicken.
c. The sheep leaps over the chicken that the fish is catching.
d. The sheep leaps over the chicken that is catching the fish.

7/32
1. The mole is chasing the ant who is little.
a. The mole is chasing the ant who is little.
b. The ant is chasing the mole who is big.
c. The mole is chasing the ant who is big.
d. The ant is chasing the mole who is little.
2. The hen is kissing the chicken who is sad.
a. The hen is kissing the chicken who is sad.
b. The chicken is kissing the hen who is happy.
c. The hen is kissing the chicken who is happy.
d. The chicken is kissing the hen who is sad.
3. The duck is drawing the mole who is asleep.
a. The duck is drawing the mole who is asleep.
b. The mole is drawing the duck who is awake.
c. The duck is drawing the mole who is awake.
d. The mole is drawing the duck who is asleep.
4. The chicken is following the sheep that is leaping.
a. The chicken is following the sheep that is leaping.
b. The sheep is following the chicken that is walking.
c. The chicken is following the sheep that is walking.
d. The sheep is following the chicken that is leaping.

Round Four Questions
3/10
1. Foxy Loxy is examining Chicken Licken.
a. Foxy Loxy is examining Chicken Licken.
b. Chicken Licken is examining Foxy Loxy.
c. Foxy Loxy is examining the radio.
2. Henny Penny is watching the fish.
a. Henny Penny is watching the fish.
b. The fish is watching Henny Penny.
c. Henny Penny is watching television.
3. The acorn is sitting on a leaf.
a. The acorn is sitting on a leaf.
b. A leaf is sitting on the acorn.
c. The acorn is sitting on Chicken Licken's head.
4. Henny Penny is kicking Foxy Loxy.
a. Henny Penny is kicking Foxy Loxy.
d. Foxy Loxy is kicking Henny Penny.
c. Henny Penny is kicking an acorn.

4/17
1. What is the acorn sitting on? (leaf)
a. What is the acorn sitting on? (leaf)
b. What is the leaf sitting on? (acorn)
c. What is the butterfly sitting on? (acorn)
2. Whom is Henny Penny kicking? (Foxy Loxy)
a. Whom is Henny Penny kicking? (Foxy Loxy)
b. Whom is Foxy Loxy kicking? (Henny Penny)
c. Whom is Chicken Licken kicking? (Henny Penny)
3. What is the caterpillar holding? (leaf)
a. What is the caterpillar holding? (leaf)
b. What is the leaf holding? (caterpillar)
c. What is the bird holding? (caterpillar)
4. Whom is Loosey Goosey carrying? (Chicken Licken)
a. Whom is Loosey Goosey carrying? (Chicken Licken)
b. Whom is Chicken Licken carrying? (Loosey Goosey)
c. Whom is Foxy Loxy carrying? (Loosey Goosey)
1. The fish is swimming upside down.
a. The fish is swimming upside down.
b. The fish are swimming upside down.
2. The fish is blowing bubbles.
a. The fish is blowing bubbles.
b. The fish are blowing bubbles.
3. The fish is making faces.
a. The fish is making faces.
b. The fish are making faces.
4. The fish is doing push-ups.
a. The fish is doing push-ups.
b. The fish are doing push-ups.

5/24
1. Foxy Loxy put a bandage on Chicken Licken.
a. Foxy Loxy put a bandage on Chicken Licken.
b. Foxy Loxy is putting a bandage on Chicken Licken.
c. Foxy Loxy will put a bandage on Chicken Licken.
2. Henny Penny turned on the radio.
a. Henny Penny turned on the radio.
b. Henny Penny is turning on the radio.
c. Henny Penny will turn on the radio.
3. Loosey Goosey jumped into his police car.
a. Loosey Goosey jumped into his police car.
b. Loosey Goosey will jump into his police car.
c. Loosey Goosey is jumping into his police car.
4. Henny Penny opened the door.
a. Henny Penny opened the door.
b. Henny Penny will open the door.
c. Henny Penny is opening the door.

5/25
1. The fish are singing.
a. The fish are singing.
b. The fish is singing.
2. The fish are dancing.
a. The fish are dancing.
b. The fish is dancing.
3. The fish are drumming.
a. The fish are drumming.
b. The fish is drumming.
4. The fish are strumming.
a. The fish are strumming.
b. The fish is strumming.

3/12
1. The grinning fox is hugging the hen.
a. The grinning fox is hugging the hen.

b. The frowning hen is hugging the fox.
c. The frowning fox is hugging the hen.
d. The grinning hen is hugging the fox.
2. The big goose is carrying the chicken.
a. The big goose is carrying the chicken.
b. The little chicken is carrying the goose.
c. The little goose is carrying the chicken.
d. The big chicken is carrying the goose.
3. The angry hen is kicking the fox.
a. The angry hen is kicking the fox.
b. The happy fox is kicking the hen.
c. The happy hen is kicking the fox.
d. The angry fox is kicking the hen.
4. The frightened chicken is hugging the goose.
a. The frightened chicken is hugging the goose.
b. The happy goose is hugging the chicken.
c. The happy chicken is hugging the goose.
d. The frightened goose is hugging the chicken.
1. The fish that the hen is watching is blowing bubbles.
a. The fish that the hen is watching is blowing bubbles.
b. The fish that the hen is watching is blowing his nose.
c. The hen that the fish is watching is blowing bubbles.
d. The hen that the fish is watching is blowing her nose.
2. The hen that the fish is watching, is watching the fox.
a. The hen that the fish is watching, is watching the fox.
b. The fish that the hen is watching, is watching the fox.
c. The fox that the hen is watching, is watching the fish.
d. The fox that the fish is watching, is watching the hen.
3. The chicken that the goose is carrying is frightened.
a. The chicken that the goose is carrying is frightened.
b. The chicken that the goose is carrying is happy.
c. The goose that the chicken is carrying is frightened.
d. The goose that the chicken is carrying is happy.
4. The acorn that the leaf is covering is brown.
a. The acorn that the leaf is covering is brown.
b. The acorn that the leaf is covering is green.
c. The leaf that the acorn is covering is brown.
d. The leaf that the acorn is covering is green.
8/39
1. The chicken is not being examined by the fox.
a. The chicken is not being examined by the fox.
b. The fox is not being examined by the chicken.
2. The chicken is not being struck by the acorn.
a. The chicken is not being struck by the acorn.
b. The acorn is not being struck by the chicken.
3. The fish is not being watched by the hen.
a. The fish is not being watched by the hen.
b. The hen is not being watched by the fish.
4. The acorn is not being struck by the leaf.
a. The acorn is not being struck by the leaf.
b. The leaf is not being struck by the acorn.
4. The acorn did not fall far from the tree.
a. The acorn did not fall far from the tree.
b. The tree did not fall far from the acorn.
has been changed to:
4. The acorn is not being struck by the leaf.
a. The acorn is not being struck by the leaf.
b. The leaf is not being struck by the acorn.

THE BIG BAD PIGS

Round One Questions: 3/7, 3/11, 3/15, 4/18, 4/21, 5/26, 5/28, 8/38

3/7
1. The wolf sees the pigs shouting.
a. The wolf sees the pigs shouting.
b. The wolf sees the pig shouting.
2. The pig is holding the brick.
a. The pig is holding the brick.
b. The pig is holding the bricks.
3. The pig is throwing the stick.
a. The pig is throwing the stick.
b. The pig is throwing the sticks.
4. The wolf is covering his ears.
a. The wolf is covering his ears.
b. The wolf is covering his ear.
3/11
1. Who is more angry?
a. Who is more angry?
b. Who is less angry?
2. Who is more slender?
a. Who is more slender?
b. Who is less slender?
3. Who is more furry?
a. Who is more furry?
b. Who is less furry?
4. Who is more noisy?
a. Who is more noisy?
b. Who is less noisy?
3/15
1. The pig is bigger.
a. The pig is bigger.
b. The pig is smaller.
2. The pig is fatter.
a. The pig is fatter.
b. The pig is thinner.
3. The wolf is taller.
a. The wolf is taller.
b. The wolf is shorter.
4. The pig is dressier.
a. The pig is dressier.
b. The pig is messier.
4/18
1. Pinky Pig holds some. (bricks)
a. Pinky holds some. (bricks)
b. Pinky Pig holds one.
c. Pinky Pig holds many.
d. Pinky Pig holds none.
2. Paddle Pig balances none. (sticks) (belongs to grammar group 3/8—was Q2)
a. Paddle Pig balances none.
b. Paddle Pig balances some. (sticks)
c. Paddle Pig balances many.
d. Paddle Pig balances one.
3. Punk Pig juggles some. (bricks)
a. Punk Pig juggles some. (bricks)
b. Punk Pig juggles none.
c. Punk Pig juggles one.
d. Punk Pig juggles many.
4. Pinky Pig sits on none.
a. Pinky Pig sits on none. (bricks)
b. Pinky Pig sits on one.
c. Pinky Pig sits on many.

d. Pinky Pig sits on some.

4/21
1. The Wolf is eating a pea.
a. The wolf is eating a pea.
b. The wolf is eating some peas.
2. Paddle Pig's sailor suit has some stripes.
a. Paddle Pig's sailor suit has some stripes.
b. Paddle Pig's sailor suit has a stripe.
3. Punk Pig wears an earring.
a. Punk Pig wears an earring.
b. Punk Pig wears some earrings.
4. Some pigs are yelling at the wolf.
a. Some pigs are yelling at the wolf.
b. A pig is yelling at the wolf.

5/26
1. She is throwing bricks.
a. She is throwing bricks.
b. He is throwing bricks.
c. They are throwing bricks.
2. She is juggling sticks.
a. She is juggling sticks.
b. He is juggling sticks.
c. They are juggling sticks.
3. He is poking the wolf.
a. He is poking the wolf.
b. They are poking the wolf.
c. She is poking the wolf.
4. They are jumping in straw.
a. They are jumping in straw.
b. She is jumping in straw.
c. He is jumping in straw.

6/28
1. Which is the baby's pig?
a. Which is the baby's pig?
b. Which is the baby pig?
2. Which is the wolf's coat?
a. Which is the wolf's coat?
b. Which is the wolf coat?
3. Which is the giant pig?
a. Which is the giant pig?
b. Which is the giant's pig?
4. Which is the wolf's rug?
a. Which is the wolf's rug?
b. Which is the wolf rug?

8/38
1. It's the straw that the pig holds.
a. It's the straw that the pig holds.
b. It's the pig that the straw holds.
c. It's the wolf that the straw holds.
d. It's the wolf that the pig holds.
2. It's the bug that the pig bites.
a. It's the bug that the pig bites.
b. It's the pig that the bug bites.
c. It's the wolf that the pig bites.
d. It's the wolf that the bug bites.
3. It's the pig that the wolf pokes.
a. It's the pig that the wolf pokes.
b. It's the wolf that the pig pokes.
c. It's the bug that the wolf pokes.
d. It's the bug that the pig pokes.
4. It's the wolf that the pig flattens. (by sitting on him)
a. It's the wolf that the pig flattens.
b. It's the pig that the wolf flattens.
c. It's the bug that the wolf flattens.
d. It's the bug that the pig flattens.

Round Two Questions: 3/13, 4/22, 5/23, 5/24, 6/30, 6/31, 7/34, 8/35

1. The pig that is in the boat does not have a hammer.
a. The pig that is in the boat does not have a hammer.
b. The pig that is in the boat has a hammer.
c. The pig that is not on the boat does not have a hammer.
d. The pig that is not in the boat has a hammer.
2. The pig that is not smiling is dropping a brick.
a. The pig that is not smiling is dropping a brick.
b. The pig that is not smiling is not dropping a brick.
c. The pig that is smiling is dropping a brick.
d. The pig that is smiling is not dropping a brick.
3. The pig that does not have a hat is in the mud.
a. The pig that does not have a hat is in the mud.
b. The pig that has a hat is in the mud.
c. The pig that has a hat is not in the mud.
d. The pig that does not have a hat is not in the mud.
4. The pig that is on the ladder does not have a bucket.
a. The pig that is on the ladder does not have a bucket.
b. The pig that is on the ladder has a bucket.
c. The pig that is not on the ladder has a bucket.
d. The pig that is not on the ladder does not have a bucket.

4/22
1. The sheep is reading in bed.
a. The sheep is reading in bed.
b. The sheep are reading in bed.
2. The fish is jumping over the pig.
a. The fish is jumping over the pig.
b. The fish are jumping over the pig.
3. The sheep is asleep.
a. The sheep is asleep.
b. The sheep are asleep.
4. The fish is in a dish.
a. The fish is in a dish.
b. The fish are in a dish.

5/23
1. The brick house is built for Pinky Pig.
a. The brick house is built for Pinky Pig.
b. The brick house is built with Pinky Pig.
c. The brick house is built by Pinky Pig.
2. The sticks are carried for Paddle Pig.
a. The sticks are carried for Paddle Pig.
b. The sticks are carried with Paddle Pig.
c. The sticks are carried by Paddle Pig.
3. The straw is tied together for Punk Pig.
a. The straw is tied together for Punk Pig.
b. The straw is tied together by Punk Pig.
c. The straw is tied together with Punk Pig.
4. The fish is caught for Paddle Pig.
a. The fish is caught for Paddle Pig.
b. The fish is caught with Paddle Pig.
c. The fish is caught by Paddle Pig.

5/24
1. Paddle Pig hammered her hand.
   a. Paddle Pig hammered her hand.
   b. Paddle Pig is hammering her hand.
   c. Paddle Pig will hammer her hand.
2. Pinky Pig fell off the ladder.
   a. Pinky Pig fell off the ladder.
   b. Pinky Pig is falling off the ladder.
   c. Pinky Pig will fall off the ladder.
3. Paddle Pig jumped into the pond.
   a. Paddle Pig jumped into the pond.
   b. Paddle Pig will jump into the pond.
   c. Paddle Pig is jumping into the pond.
4. Punk Pig got muddy.
   a. Punk Pig got muddy.
   b. Punk Pig will get muddy.
   c. Punk Pig is getting muddy.

6/30
1. The pig who is chasing the fish that is frightened is happy.
   a. The pig who is chasing the fish that is frightened is happy.
   b. The pig who is chasing the fish that is happy is frightened.
   c. The pig who is chasing the fish that is happy is happy.
   d. The pig who is chasing the fish that is frightened is frightened.
2. The pig who is wearing the hat that is little is big.
   a. The pig who is wearing the hat that is little is big.
   b. The pig who is wearing the hat that is big is little.
   c. The pig who is wearing the hat that is big is big.
   d. The pig who is wearing the hat that is little is little.
3. The bug who is biting the pig who has a hat has wings.
   a. The bug who is biting the pig who has a hat has wings
   b. The bug who is biting the pig who has wings has a hat.
   c. The bug who is biting the pig who has a hat has a hat.
   d. The bug who is biting the pig who has wings has wings.
4. The wolf who is watching the pig on the roof is on the ground.
   a. The wolf who is watching the pig on the roof is on the ground.
   b. The wolf who is watching the pig on the ground is on the roof.
   c. The wolf who is watching the pig on the roof is on the roof.
   d. The wolf who is watching the pig on the ground is on the ground.

6/31
1. The pig building the house that is red is pink. (brick house)
   a. The pig building the house that is red is pink.
   b. The pig building the house that is red is red.
   c. The pig building the house that is pink is red.
   d. The pig building the house that is pink is pink.
2. The pig scaring the fish that is swimming is jumping.
   a. The pig scaring the fish that is swimming is jumping.
   b. The pig scaring the fish that is swimming is swimming.
   c. The pig scaring the fish that is jumping is swimming.
   d. The pig scaring the fish that is jumping is jumping.
3. The wolf wearing a tie that is striped is furry.
   a. The wolf wearing a tie that is striped is furry.
   b. The wolf wearing a tie that is striped is striped.
   c. The wolf wearing a tie that is furry is striped.
   d. The wolf wearing a tie that is furry is furry.
4. The pig sitting in mud that is brown is purple.
   a. The pig sitting in mud that is brown is purple.
   b. The pig sitting in mud that is brown is brown.
   c. The pig sitting in mud that is purple is brown.
   d. The pig sitting in mud that is purple is purple.

7/34
1. What is on the ladder? (a bucket of bricks)
   a. What is on the ladder? (a bucket of bricks)
   b. Who is on the ladder? (Pinky Pig)
   c. Is nothing on the ladder?
2. Who is in the mud? (Punk Pig)
   a. Who is in the mud? (Punk Pig)
   b. What is in the mud? (ladder? bucket?)
   c. Is nothing in the mud?
3. Who is in the bucket? (Pinky Pig)
   a. Who is in the bucket? (Pinky Pig)
   b. What is in the bucket? (bricks)
   c. Is nothing in the bucket?
4. What is on the roof? (a box of nails—stick house)
   a. What is on the roof? (a box of nails—stick house)
   b. Who is on the roof? (Party Pig, hammering)
   c. Is nothing on the branch?

8/35 (Note that 8/35 and 4/19 are intermingled across rounds 2 & 4)
1. The sheep creep.
   a. The sheep creep.
   b. The sheep creeps.
2. The fish fries. (belongs in grammar group 4/19—was Q2)
   a. The fish fries.
   b. The fish fry.
3. The sheep weep.
   a. The sheep weep.
   b. The sheep weeps.
4. The fish crashes. (belongs in grammar group 4/19—was Q4)
   a. The fish crashes.
   b. The fish crash.

8/35 2. The fish fry.
   a. The fish fry.
   b. The fish fries.

Round Three Questions: 3/8, 3/9, 3/12, 4/16, 4/17, 7/33, 8/36, 8/37

1. The box has none. (nails)
   a. The box has none. (nails)
   b. The box has many.
   c. The box has some.
   d. The box has one.
2. The pig drops some. (bricks) (belongs to grammar group 4/18—was Q2)
   a. The pig drops some. (bricks)
   b. The pig drops one.
   c. The pig drops none.
   d. The pig drops many.
3. The pig catches none. (fish)

a. The pig catches none. (fish)
b. The pig catches some.
c. The pig catches one.
d. The pig catches many.
4. The wolf eats some. (peas)
a. The wolf eats some. (peas)
b. The wolf eats many.
c. The wolf eats one.
d. The wolf eats none.

3/9
1. The pig who is angry is slugging the wolf.
a. The pig who is angry is slugging the wolf.
b. The wolf who is angry is slugging the pig.
c. The pig who is happy is slugging the wolf.
d. The wolf who is happy is slugging the pig.
2. The pig who is happy is hugging the wolf.
a. The pig who is happy is hugging the wolf.
b. The wolf who is happy is hugging the pig.
c. The pig who is angry is hugging the wolf.
d. The wolf who is angry is hugging the pig.
3. The house that is yellow is falling on the pig.
a. The house that is yellow is falling on the pig.
b. The pig that is yellow is falling on the house.
c. The house that is purple is falling on the pig.
d. The pig that is purple is falling on the house.
4. The pig with the hat is kicking the wolf.
a. The pig with the hat is kicking the wolf.
b. The wolf with the hat is kicking the pig.
c. The pig with the tie is kicking the wolf.
d. The wolf with the tie is kicking the pig.

3/12
1. The pink pig is licking the wolf.
a. The pink pig is licking the wolf.
b. The gray wolf is licking the pig.
c. The gray pig is licking the wolf.
d. The pink wolf is licking the pig.
2. The tiny bug is biting the pig.
a. The tiny bug is biting the pig.
b. The tiny pig is biting the bug.
c. The giant bug is biting the pig.
d. The giant pig is biting the bug.
3. The angry wolf is chasing the pig.
a. The angry wolf is chasing the pig.
b. The happy pig is chasing the wolf.
c. The happy wolf is chasing the pig.
d. The angry pig is chasing the wolf.
4. The frightened fish is hiding from the pig.
a. The frightened fish is hiding from the pig.
b. The happy pig is hiding from the fish.
c. The happy fish is hiding from the pig.
d. The frightened pig is hiding from the fish.

4/16
1. The wolf is being kicked by the pig.
a. The wolf is being kicked by the pig.
b. The pig is being kicked by the wolf.
c. The wolf is being kicked by the bug.
d. The bug is being kicked by the pig.
2. The house is being flattened by the wolf.
a. The house is being flattened by the wolf.
b. The wolf is being flattened by the house.
c. The house is being flattened by the pig.
d. The pig is being flattened by the wolf.
3. The water is splashing into the bucket.
a. The water is splashing into the bucket.
b. The bucket is splashing into the water.
c. The water is splashing into the mud.
d. The mud is splashing into the bucket.
4. The pig is being chased by the wolf.
a. The pig is being chased by the wolf.
b. The wolf is being chased by the pig.
c. The pig is being chased by the fish.
d. The fish is being chased by the wolf.

4/17
1. What is the brick hitting? (the mud)
a. What is the brick hitting? (the mud)
b. What is the mud hitting? (the brick)
c. What is the pig hitting? (the brick)
2. Whom is Punk Pig punching? (the wolf)
a. Whom is Punk Pig punching? (the wolf)
b. Whom is the wolf punching? (Punk Pig)
c. Whom is the bug punching? (Punk Pig)
3. What is the rope holding? (straw)
a. What is the rope holding? (straw)
b. What is the straw holding? (rope)
c. What is the pig holding? (rope)
4. Whom is Paddle Pig chasing? (a fish)
a. Whom is Paddle Pig chasing? (a fish)
b. Whom is the fish chasing? (Paddle Pig)
c. Whom is the wolf chasing? (Paddle Pig)

7/33
1. The boat sitting in the water is yellow.
a. The boat sitting in the water is yellow.
b. The water sitting in the boat is yellow.
c. The boat sitting in the water is blue.
d. The water sitting in the boat is blue.
3. The pig slugging the wolf is shouting.
a. The pig slugging the wolf is shouting.
b. The wolf slugging the pig is shouting.
c. The pig slugging the wolf is silent.
d. The wolf slugging the pig is silent.
3. The sheep leaping over the pig is weeping.
a. The sheep leaping over the pig is weeping.
b. The pig leaping over the sheep is weeping.
c. The sheep leaping over the pig is laughing.
d. The pig leaping over the sheep is laughing.
4. The pig landing on the roof is pink.
a. The pig landing on the roof is pink.
b. The roof landing on the pig is pink.
c. The pig landing on the roof is brown.
d. The roof landing on the pig is brown.

8/36
1. The stick that the brick is hitting is broken.
a. The stick that the brick is hitting is broken.
b. The stick that the brick is hitting is not broken.
c. The brick that the stick is hitting is broken.
d. The brick that the stick is hitting is not broken.
2. The pig that the bug is biting, is biting the wolf.
a. The pig that the bug is biting, is biting the wolf.

b. The bug that the pig is biting, is biting the wolf.
c. The wolf that the pig is biting, is biting the bug.
d. The pig that the wolf is biting, is biting the bug.
3. The pig that the wolf is watching is hammering her hand.
a. The pig that the wolf is watching is hammering her hand.
b. The pig that the wolf is watching is hammering a nail.
c. The wolf that the pig is watching is hammering his thumb.
d. The wolf that the pig is watching is hamering a nail.
4. The pig that the straw is holding is muddy.
a. The pig that the straw is holding is muddy.
b. The pig that the straw is holding is clean.
c. The straw that the pig is holding is muddy.
d. The straw that the pig is holding is clean.

8/37
1. The bug is slugging the wolf that the pig is hugging.
a. The bug is slugging the wolf that the pig is hugging.
b. The bug is slugging the wolf that is hugging the pig.
c. The bug is slugging the pig that the wolf is hugging.
d. The bug is slugging the pig that is hugging the wolf.
2. The pig is kicking the wolf that the sheep is licking.
a. The pig is kicking the wolf that the sheep is licking.
b. The pig is kicking the wolf that is licking the sheep.
c. The pig is kicking the sheep that the wolf is licking.
d. The pig is kicking the sheep that is lickling the wolf.
3. The mud is covering the pig that the bug is biting.
a. The mud is covering the pig that the bug is biting.
b. The mud is covering the pig that is biting the bug.
c. The mud is covering the bug that the pig is biting.
d. The mud is covering the bug that is biting the pig.
4. The fish is landing on the pig that the boat is carrying.
a. The fish is landing on the pig that the boat is carrying.
b. The fish is landing on the pig that is carrying the boat.
c. The fish is landing on the boat that the pig is carrying.
d. The fish is landing the boat that is carrying the pig.

Round Four Questions: 3/10, 4/19, 4/20, 5/25, 6/27, 6/29, 7/32, 8/39

1. The pig is throwing an egg at the wolf.
a. The pig is throwing an egg at the wolf.
b. The wolf is throwing an egg at the pig.
c. The pig is throwing an egg at the bug.
2. The hammer is breaking the brick.
a. The hammer is breaking the brick.
b. The brick is breaking the hammer.
c. The hammer is breaking the egg.
3. Pinky Pig is sitting on the roof.
a. Pinky Pig is sitting on the roof.
b. The roof is sitting on Pinky Pig.
c. Pinky Pig is sitting on a rock.
4. Pinky Pig is licking the wolf.
a. Pinky Pig is licking the wolf.
d. The wolf is licking Pinky Pig.
c. Pinky Pig is licking a lollypop.

4/19
1. The beaver carries the sticks.
a. The beaver carries the sticks.
b. The beaver carry the sticks.
2. The fish paddle the boat. (belongs to grammar group 8/36—was Q2)
a. The fish paddle the boat.
b. The fish paddles the boat.
3. The sheep shaves.
a. The sheep shaves.
b. The sheep shave.
4. The fish fish. (belongs to grammar group 8/35—was Q4)
a. The fish fish.
b. The fish fishes.

4/20
1. The pig is climbing the ladder.
a. The pig is climbing the ladder.
b. The pig climbed the ladder.
c. The pig will climb the ladder.
2. The pig is catching the bug.
a. The pig is catching the bug.
b. The pig caught the bug.
c. The pig will catch the bug.
3. The wolf is blowing down the house.
a. The wolf is blowing down the house.
b. The wolf blew down the house.
c. The wolf will blow down the house.
4. The tomato is hitting the wolf.
a. The tomato is hitting the wolf.
b. The tomato hit the wolf.
c. The tomato will hit the wolf.

5/25
1. The sheep are eating straw.
a. The sheep are eating straw.
b. The sheep is eating straw.
2. The fish are rowing the boat.
a. The fish are rowing the boat.
b. The fish is rowing the boat.
3. The beaver are stacking sticks.
a. The beaver are stacking sticks.
b. The beaver is stacking sticks.
4. The sheep are chasing the pig.
a. The sheep are chasing the pig.
b. The sheep is chasing the pig.

6/27
1. The pig will eat the bug.
a. The pig will eat the bug.
b. The pig ate the bug.
c. The pig is eating the bug.
2. The wolf will fall in the mud.
a. The wolf will fall in the mud.
b. The wolf is falling in the mud.
c. The wolf fell in the mud.
3. The house will fall down.
a. The house will fall down.
b. The house is falling down.
c. The house fell down.
4. The boat will sink.
a. The boat will sink.
b. The boat is sinking.
c. The boat sank.

6/29
1. The pig is falling with the ladder.
   a. The pig is falling with the ladder.
   b. The pig is falling to the ladder.
   c. The pig is falling from the ladder.
2. The fish is swimming with the pig.
   a. The fish is swimming with the pig
   b. The fish is swimming to the pig.
   c. The fish is swimming from the pig.
3. The sheep is running with the wolf.
   a. The sheep is running with the wolf.
   b. The sheep is running to the wolf.
   c. The sheep is running from the wolf.
4. The beaver is carrying sticks with the pig.
   a. The beaver is carrying sticks with the pig.
   b. The beaver is carrying sticks to the pig.
   c. The beaver is carrying sticks from the pig.

7/32
1. The wolf is watching the sheep who is sleeping.
   a. The wolf is watching the sheep who is sleeping.
   b. The sheep is watching the wolf who is dancing.
   c. The wolf is watching the sheep who is dancing.
   d. The sheep is watching the wolf who is sleeping.
2. The pig is throwing an egg at the wolf who is walking.
   a. The pig is throwing an egg at the wolf who is walking.
   b. The wolf is throwing an egg at the pig who is walking.
   c. The pig is throwing an egg at the wolf who is running.
   d. The wolf is throwing an egg at the pig who is running.
3. The pig is jumping over the fish who is paddling. (the boat)
   a. The pig is jumping over the fish who is paddling.
   b. The fish is jumping over the pig who is paddling.
   c. The pig is jumping over the fish who is jumping.
   d. The fish is jumping over the pig who is jumping.
4. The beaver is biting the sheep who is weeping.
   a. The beaver is biting the sheep who is weeping.
   b. The sheep is biting the beaver who is weeping.
   c. The beaver is biting the sheep who is eating.
   d. The sheep is biting the beaver who is eating.

8/39
1. The fish is not being caught by the pig.
   a. The fish is not being caught by the pig.
   b. The fish is not being caught by the wolf.
   c. The pig is not being caught by the fish.
2. The wolf is not being kicked by the pig.
   a. The wolf is not being kicked by the pig.
   b. The wolf is not being kicked by the sheep.
   c. The pig is not being kicked by the wolf.
3. The pig is not being struck by the falling bucket.
   a. The pig is not being struck by the falling bucket.
   b. The pig is not being struck by the falling brick.
   c. The bucket is not being struck by the falling pig.
4. The straw is not being covered by the sheep.
   a. The straw is not being covered by the sheep.
   b. The sheep is not being covered by the straw.

LITTLE RED AND THE WOLF

Round One Questions: 3/8, 3/15, 4/20, 4/21, 5/23, 6/27, 7/34, 8/38

1. The cape has none. (buttons)
   a. The cape has none. (buttons)
   b. The cape has many.
   c. The cape has some.
   d. The cape has one.
2. Little Red's face has none. (bandages)
   a. Little Red's face has none. (bandages)
   b. Little Red's face has one.
   c. Little Red's face has some.
   d. Little Red's face has many.
3. The basket has none. (treaties-varying objects, can be wrapped)
   a. The basket has none. (treaties)
   b. The basket has some.
   c. The basket has one.
   d. The basket has many.
4. The bed has none. (socks strewn on it)
   a. The bed has none. (socks strewn on it))
   b. The bed has many.
   c. The bed has one.
   d. The bed has some.

3/15
1. The girl is angrier.
   a. The girl is angrier.
   b. The girl is happier.
2. The boots are older.
   a. The boots are older.
   b. The boots are newer.
3. The basket is bigger.
   a. The basket is bigger.
   b. The basket is smaller.
4. The mother has longer hair.
   a. The mother has longer hair.
   b. The mother has shorter hair.

4/20
1. Little Red is throwing her cape into the trash.
   a. Little Red is throwing her cape into the trash.
   b. Little Red threw her cape into the trash.
   c. Little Red will throw her cape into the trash.
2. Little Red is uncovering the basket.
   a. Little Red is uncovering the basket.
   b. Little Red uncovered the basket.
   c. Little Red will uncover the basket.
3. Little Red is putting on the cape.
   a. Little Red is putting on the cape.
   b. Little Red put on the cape.
   c. Little Red will put on the cape.
4. Little Red is crying.
   a. Little Red is crying.
   b. Little Red cried.
   c. Little Red will cry.

4/21
1. Little Red has a ribbon in her hair.
   a. Little Red has a ribbon in her hair.
   b. Little Red has some ribbons in her hair.
2. Little Red's cape has some patches.
   a. Little Red's cape has some patches.
   b. Little Red's cape has a patch.
3. Little Red's mother has a basket. (I wanted to say, 'tattoo.')
   a. Little Red's mother has a basket.
   b. Little Red's mother has some baskets.

4. Some dolls are on Little Red's bed.
a. Some dolls are on Little Red's bed.
b. A doll is on Little Red's bed.

5/23
1. The cape is made for Little Red.
a. The cape is made for Little Red.
b. The cape is made with Little Red.
c. The cape is made by Little Red.
2. The basket is filled for Granny.
a. The basket is filled for Granny.
b. The basket is filled with Granny.
c. The basket is filled by Granny.
3. The boots are tied for Little Red.
a. The boots are tied for Little Red.
b. The boots are tied with Little Red.
c. The boots are tied by Little Red.
4. The bed is made for Little Red.
a. The bed is made for Little Red.
b. The bed is made with Little Red.
c. The bed is made by Little Red.

6/27
1. Little Red will kick over the trash can.
a. Little Red will kick over the trash can.
b. Little Red kicked over the trash can.
c. Little Red is kicking over the trash can.
2. The mother will take off her glasses.
a. The mother will take off her glasses.
b. The mother is taking off her glasses.
c. The mother took off her glasses.
3. Little Red will crawl under the bed.
a. Little Red will crawl under the bed.
b. Little Red is crawling under the bed.
c. Little Red crawled under the bed.
4. The basket will fall.
a. The basket will fall.
b. The basket is falling.
c. The basket fell.
1. What is in the trash can? (the red cape)
a. What is in the trash can? (the red cape)
b. Who is in the trash can? (Little Red)
c. Is nothing in the trash can?
2. Who is in the doorway? (Little Red's mother)
a. Who is in the doorway? (Little Red's mother)
b. What is in the doorway? (a basket)
c. Is nothing in the doorway?
3. Who is on the bed? (Little Red)
a. Who is on the bed? (Little Red)
b. What is on the bed? (socks)
c. Is nothing on the bed?
4. What is in the basket? (treaties)
a. What is in the basket? (treaties)
b. Who is in the basket? (Granny)
c. Is nothing in the basket?

8/38
1. It's the basket that the mother holds.
a. It's the basket that the mother holds.
b. It's the mother that the basket holds.
c. It's Little Red that the basket holds.
d. It's Little Red that the mother holds.
2. It's Little Red that the cape covers.
a. It's Little Red that the cape covers.
b. It's the cape that Little Red covers.
c. It's the trash can that the cape covers.
d. It's the trash can that Little Red covers.
3. It's the mother that the little girl scolds.
a. It's the mother that the little girl scolds.
b. It's the little girl that the mother scolds.
c. It's Granny that the little girl scolds.
d. It's Granny that the mother scolds.
4. It's the bed that the blanket covers.
a. It's the bed that the blanket covers.
b. It's the blanket that the bed covers.
c. It's Little Red that the bed covers.
d. It's Little Red that the blanket covers.

4/21/2.
Little Red's cape has some patches.
a. Little Red's cape has some patches.
b. Little Red's cape has a patch.

3/8
2. Little Red's face has none. (bandages)
a. Little Red's face has none. (bandages)
b. Little Red's face has one.
c. Little Red's face has some.
d. Little Red's face has many.

3/15
b 2. The boots are older.
a. The boots are older.
b. The boots are newer.

4/20
2. Little Red is uncovering the basket.
a. Little Red is uncovering the basket.
b. Little Red uncovered the basket.
c. Little Red will uncover the basket.

6/27
1. Little Red will kick over the trash can.
a. Little Red will kick over the trash can.
b. Little Red kicked over the trash can.
c. Little Red is kicking over the trash can.
2. The mother will take off her glasses.
a. The mother will take off her glasses.
b. The mother is taking off her glasses.
c. The mother took off her glasses.

Round Two Questions: 3/7, 3/13, 4/17, 4/19, 5/25, 6/29, 7/32, 8/35

3/7
1. Little Red is kicking the rock.
a. Little Red is kicking the rock.
b. Little Red is kicking the rocks.
2. The wolf is behind the tree.
a. The wolf is behind the tree.
b. The wolf is behind the trees.
3. Little Red dances with the wolves.
a. Little Red dances with the wolves.
b. Little Red dances with the wolf.
4. The wolf holds the baskets.
a. The wolf holds the baskets.
b. The wolf holds the basket.

3/13
1. The girl that is wearing a cape does not have a basket.
a. The girl that is wearing a cape does not have a basket.
b. The girl that is wearing a cape has a basket.
c. The girl that is not wearing a cape does not have a basket.
d. The girl that is not wearing a cape has a basket.
2. The wolf that is not wearing a jacket is wearing boots.
a. The wolf that is not wearing a jacket is wearing boots.
b. The wolf that is wearing a jacket is wearing boots.
c. The wolf that is wearing a jacket is not wearing boots.
d. The wolf that is not wearing a jacket is not wearing boots.
3. The girl that is frowning is not running.
a. The girl that is frowning is not running.
b. The girl that is frowning is running.
c. The girl that is not frowning is running.
d. The girl that is not frowning is not running.
4. The wolf that is not chasing the bird is drooling.
a. The wolf that is not chasing the bird is drooling.
b. The wolf that is not chasing the bird is not drooling.
c. The wolf that is chasing the bird is drooling.
d. The wolf that is chasing the bird is not drooling.
4/17
1. What is Little Red holding? (the basket)
a. What is Little Red holding? (the basket)
b. What is the basket holding? (Little Red)
c. What is the wolf holding? (Little Red)
2. Whom is the bird watching? (the wolf, with binoculars)
a. Whom is the bird watching? (the wolf)
b. Whom is the wolf watching? (the bird, with binoculars)
c. Whom is Little Red watching? (the bird, with binoculars)
3. What does the basket cover? (the napkin)
a. What does the basket cover? (the napkin)
b. What does the napkin cover? (the basket)
c. What does the wolf cover? (the basket)
4. To whom is the wolf whispering? (Little Red)
a. To whom is the wolf whispering? (Little Red)
b. To whom is Little Red whispering? (the wolf)
c. To whom is the bird whispering? (the wolf)
4/19
1. The deer eats leaves.
a. The deer eats leaves.
b. The deer eat leaves.
2. The fish jumps in the stream. (not 'into')
a. The fish jumps in the stream.
b. The fish jump in the stream.
3. The deer leaps over the log.
a. The deer leaps over the log.
b. The deer leap over the log.
4. The fish feeds the fish.
a. The fish feeds the fish.
b. The fish feed the fish.
5/25
1. The deer are eating pizza.
a. The deer are eating pizza.
b. The deer is eating pizza.
2. The fish are wearing glasses.
a. The fish are wearing glasses.
b. The fish is wearing glasses.
3. The deer are wearing boots.
a. The deer are wearing boots.
b. The deer is wearing boots.
4. The fish are out of water.
a. The fish are out of water.
b. The fish is out of water.
5/29
1. Little Red is walking with the wolf.
a. Little Red is walking with the wolf.
b. Little Red is walking to the wolf.
c. Little Red is walking from the wolf.
2. The deer is leaping with the leaves. (with leaves in its mouth)
a. The deer is leaping with the leaves.
b. The deer is leaping to the leaves. (into a pile of leaves)
c. The deer is leaping from the leaves. (from a pile of leaves)
3. The wolf is running with the basket.
a. The wolf is running with the basket.
b. The wolf is running to the basket.
c. The wolf is running from the basket.
4. The bird is flying with the fish.
a. The bird is flying with the fish.
b. The bird is flying to the fish.
c. The bird is flying from the fish.
7/32
1. The wolf is holding the basket that is yellow.
a. The wolf is holding the basket that is yellow.
b. The basket is holding the wolf that is yellow.
d. The basket is holding the wolf that is gray.
c. The wolf is holding the basket that is gray.
2. The fish is leaping over the deer that is sleeping.
a. The fish is leaping over the deer that is sleeping.
b. The deer is leaping over the fish that is sleeping.
c. The fish is leaping over the deer that is eating.
d. The deer is leaping over the fish that is eating.
3. The wolf is following the girl wearing a cape.
a. The wolf is following the girl wearing a cape.
b. The girl is following the wolf wearing a cape.
c. The wolf is following the girl wearing glasses.
d. The girl is following the wolf wearing glasses.
4. The bird is landing on the leaf that is green.
a. The bird is landing on the leaf that is green.
b. The leaf is landing on the bird that is green.
c. The bird is landing on the leaf that is yellow.
d. The leaf is landing on the bird that is yellow.
8/35
1. The fish wish. (using a wishbone)
a. The fish wish.
b. The fish wishes.
2. The deer rear.
a. The deer rear.
b. The deer rears.
3. The fish wash a dish.
a. The fish wash a dish.
b. The fish washes a dish.
4. The deer drink root beer.
a. The deer drink root beer.
b. The deer drinks root beer.

Round Three Questions: 3/10, 3/11, 4/16, 4/22, 5/24, 5/28, 7/33, 8/39

3/10
1. Little Red is giving the basket to Granny.
a. Little Red is giving the basket to Granny.
b. Granny is giving the basket to Little Red.
c. Little Red is giving the basket to the deer.
2. Granny is lying on the bed
a. Granny is lying on the bed.
b. The bed is lying on Granny.
c. Granny is lying on the floor.
3. The goldfish is resting on the sand.
a. The goldfish is resting on the sand.
b. The sand is resting on the goldfish.
c. The goldfish is resting on the bed.
4. Granny is hugging Little Red.
a. Granny is hugging Little Red.
d. Little Red is hugging Granny.
c. Granny is hugging the pillow.

3/11
1. Whose hair is more fluffy?
a. Whose hair is more fluffy?
b. Whose hair is less fluffy?
4. Which pillow is more puffy?
a. Which pillow is more puffy?
b. Which pillow is less puffy?
2. Which bread is more crusty?
a. Which bread is more crusty?
b. Which bread is less crusty?
3. Which desk is more dusty?
a. Which desk is more dusty?
b. Which desk is less dusty?

4/16
1. The goldfish is being fed by Granny.
a. The goldfish is being fed by Granny.
b. Granny is being fed by the goldfish.
c. The goldfish is being fed by Little Red.
d. Little Red is being fed by Granny.
2. The pillow is being hit by Granny.
a. The pillow is being hit by Granny.
b. Granny is being hit by the pillow.
c. The pillow is being hit by Little Red.
d. Little Red is being hit by Granny.
3. Little Red is sitting on the pillow.
a. Little Red is sitting on the pillow.
b. The pillow is sitting on Little Red.
c. Little Red is sitting on the fish bowl.
d. The fish bowl is sitting on the pillow.
4. The basket is being held by Granny.
a. The basket is being held by Granny.
b. Granny is being held by the basket.
c. The basket is being held by Little Red.
d. Little Red is being held by Granny.

4/22
1. The deer is at the door.
a. The deer is at the door.
b. The deer are at the door.
2. The fish is swimming in the bowl.
a. The fish is swimming in the bowl.
b. The fish are swimming in the bowl.
3. The deer is peering in the window.
a. The deer is peering in the window.
b. The deer are peering in the window.
4. The fish is in the tunnel.
a. The fish is in the tunnel.
b. The fish are in the tunnel.

5/24
1. Granny got out of bed.
a. Granny got out of bed.
b. Granny is getting out of bed.
c. Granny will get out of bed.
2. Little Red gave the basket to Granny.
a. Little Red gave the basket to Granny.
b. Little Red is giving the basket to Granny.
c. Little Red will give the basket to Granny.
3. Granny fed the goldfish.
a. Granny fed the Goldfish.
b. Granny will feed the goldfish.
c. Granny is feeding the goldfish.
4. Little Red took off the boots.
a. Little Red took off the boots.
b. Little Red will take off the boots.
c. Little Red is taking off the boots.

6/28
1. Which is the baby's goldfish?
a. Which is the baby's goldfish?
b. Which is the baby goldfish?
2. Which is the wolf's button?
a. Which is the wolfs button?
b. Which is the wolf button?
3. Which is the goldfish bowl?
a. Which is the goldfish bowl?
b. Which is the goldfish's bowl?
4. Which is the wolfs drawing?
a. Which is the wolf's drawing?
b. Which is the wolf drawing?

7/33
1. The napkin covering the basket is blue
a. The napkin covering the basket is blue.
b. The basket covering the napkin is blue.
c. The napkin covering the basket is yellow.
d. The basket covering the napkin is yellow.
3. The box inside the basket is empty.
a. The box inside the basket is empty.
b. The basket inside the box is empty.
c. The box inside the basket is full.
d. The basket inside the box is full.
3. The goldfish chasing the snail is big.
a. The goldfish chasing the snail is big.
b. The snail chasing the goldfish is big.
c. The goldfish chasing the snail is small.
d. The snail chasing the goldfish is small.
4. The flower on Granny's nightcap is yellow.
a. The flower on Granny's nightcap is yellow.
b. The nightcap on Granny's flower is yellow.
c. The flower on Granny's nightcap is purple.
d. The nightcap on Granny's flower is purple.

8/39
1. The fish is not being caught by Granny.

a. The fish is not being caught by Granny.
b. Granny is not being caught by the fish.
2. Little Red is not being followed by Granny.
a. Little Red is not being followed by Granny.
b. Granny is not being followed by Little Red.
3. The fish bowl is not being struck by the falling basket.
a. The fish bowl is not being struck by the falling basket.
b. The basket is not being struck by the falling fish bowl.
4. The snail is not being followed by the goldfish.
a. The snail is not being followed by the goldfish.
b. The goldfish is not being followed by the snail.

3/9
1. The wolf, eating bread, is pouring tea for Granny.
a. The wolf, eating bread, is pouring tea for Granny.
b. Granny, eating bread, is pouring tea for the wolf.
c. The wolf, eating a cookie, is pouring tea for Granny.
d. Granny, eating a cookie, is pouring tea for the wolf.
2. The wolf in the chair is holding the basket.
a. The wolf in the chair is holding the basket.
b. The basket in the chair is holding the wolf.
c. The wolf at the door is holding the basket.
d. The basket at the door is holding the wolf.
3. The cups that are green are below the plates.
a. The cups that are green are below the plates.
b. The plates that are green are below the cups.
c. The cups that are blue are below the plates.
d. The plates that are blue are below the cups.
4. Granny, in a cap, is sitting on the wolf's lap.
a. Granny, in a cap, is sitting on the wolf's lap.
b. The wolf, in a cap, is sitting on Granny's lap.
c. Granny, in a cape, is sitting on the wolf's lap.
d. The wolf, in a cape, is sitting on Granny's lap.

3/12
1. The spotted napkin is covering the basket.
a. The spotted napkin is covering the basket.
b. The spotted basket is covering the napkin.
c. The striped napkin is covering the basket.
d. The striped basket is covering the napkin.
2. The flowered nightcap is sitting on the pillow.
a. The flowered nightcap is sitting on the pillow.
b. The flowered pillow is sitting on the nightcap.
c. The striped nightcap is sitting on the pillow.
d. The striped pillow is sitting on the nightcap.
3. The wolf, in boots, is following Granny.
a. The wolf, in boots, is following Granny.
b. Granny, in slippers, is following the wolf.
c. The wolf, in slippers, is following Granny.
d. Granny, in boots, is following the wolf.
4. The orange fish is hiding in the tunnel from the snail.
a. The orange fish is hiding in the tunnel from the snail.
b. The blue snail is hiding in the tunnel from the fish.
c. The blue fish is hiding in the tunnel from the snail.
d. The orange snail is hiding in the tunnel from the fish.

4/18
1. The plate holds some. (cookies)
a. The plate holds some. (cookies)
b. The plate holds one.
c. The plate holds many.
d. The plate holds none.
2. Granny's nightcap has some. (flowers)
a. Granny's nightcap has some. (flowers)
b. Granny's nightcap has many.
c. Granny's nightcap has none.
d. Granny's nightcap has one.
3. The fish bowl has some. (plants)
a. The fish bowl has some. (plants)
b. The fish bowl has none.
c. The fish bowl has one.
d. The fish bowl has many.
4. Granny's kitchen sink has some. (dirty dishes)
a. Granny's kitchen sink has some. (dirty dishes)
b. Granny's kitchen sink has one.
c. Granny's kitchen sink has many.
d. Granny's kitchen sink has none.

5/26
1. She is eating a cookie.
a. She is eating a cookie.
b. He is eating a cookie.
c. They are eating cookies.
2. She is sneezing.
a. She is sneezing.
b. He is sneezing.
c. They are sneezing.
3. He is dusting.
a. He is dusting.
b. They are dusting.
c. She is dusting.
4. They are wearing boots.
a. They are wearing boots.
b. She is wearing boots.
c. He is wearing boots.

6/30
1. The wolf washing the dish that is dirty is clean.
a. The wolf washing the dish that is dirty is clean.
b. The wolf washing the dish that is clean is dirty.
c. The wolf washing the dish that is clean is clean.
d. The wolf washing the dish that is dirty is dirty.
2. The fish following the snail that is purple is orange.
a. The fish following the snail that is purple is orange.
b. The fish following the snail that is orange is purple.
c. The fish following the snail that is orange is orange.
d. The fish following the snail that is purple is purple.
3. The basket sitting on the table that is round is square.
a. The basket sitting on the table that is round is square.
b. The basket sitting on the table that is square is round.
c. The basket sitting on the table that is round is round.
d. The basket sitting on the table that is square is square.
4. The wolf sitting in the chair that is short is tall.
a. The wolf sitting in the chair that is short is tall.
b. The wolf sitting in the chair that is tall is short.
c. The wolf sitting in the chair that is short is short.
d. The wolf sitting in the chair that is tall is tall.

6/31
1. The quilt covering the bed that is blue is pink.
a. The quilt covering the bed that is blue is pink.
b. The quilt covering the bed that is pink is blue.
c. The quilt covering the bed that is blue is blue.
d. The quilt covering the bed that is pink is pink.

2. The cup sifting on the plate that is striped is flowered.
a. The cup sitting on the plate that is striped is flowered.
b. The cup sitting on the plate that is flowered is flowered.
c. The cup sitting on the plate that is flowered is striped.
d. The cup sitting on the plate that is striped is striped.
3. The wolf wearing a coat that is blue is gray.
a. The wolf wearing a coat that is blue is gray.
b. The wolf wearing a coat that is blue is blue.
c. The wolf wearing a coat that is gray is blue.
d. The wolf wearing a coat that is gray is gray.
4. The granny hugging the wolf that is crying is smiling.
a. The granny hugging the wolf that is crying is smiling.
b. The granny hugging the wolf that is crying is crying.
c. The granny hugging the wolf that is smiling is crying.
d. The granny hugging the wolf that is smiling is smiling.

8/36
1. The snail that the fish is chasing has spots.
a. The snail that the fish is chasing has spots.
b. The snail that the fish is chasing has stripes.
c. The fish that the snail is chasing has spots.
d. The fish that the snail is chasing has stripes.
2. The cape that Granny is sitting on, is on the chair.
a. The cape that Granny is sitting on, is on the chair.
b. Granny, whom the cape is sitting on, is on the chair.
c. The chair that the cape is sitting on, is on Granny.
d. The chair that the Granny is sitting on, is on the cape.
3. Granny, whom the wolf is watching, is drinking tea.
a. Granny, whom the wolf is watching, is drinking tea.
b. Granny, whom the wolf is watching, is sneezing.
c. The wolf, whom Granny is watching, is drinking tea.
d. The wolf, whom Granny is watching, is sneezing.
4. The bowl that the wolf is holding holds cookies.
a. The bowl that the wolf is holding holds cookies.
b. The bowl that the wolf is holding holds a goldfish.
c. The wolf that the bowl is holding holds cookies.
d. The wolf that the bowl is holding holds a goldfish.

8/37
1. The napkin covers the basket that the wolf is holding.
a. The napkin covers the basket that the wolf is holding.
b. The napkin covers the basket that is holding the wolf.
c. The napkin covers the wolf that the basket is holding.
d. The napkin covers the wolf that is holding the basket.
2. Granny is catching the snail that the fish is following.
a. Granny is catching the snail that the fish is following.
b. Granny is catching the snail that is following the fish.
c. Granny is catching the fish that the snail is following.
d. Granny is catching the fish that is following the snail.
3. The wolf is dusting the tablecloth that the table covers.
a The wolf is dusting the tablecloth that the table covers.
b. The wolf is dusting the table that covers the tablecloth.
c. The wolf is dusting the table that the tablecloth covers.
d. The wolf is dusting the tablecloth that covers the table.
4. Granny is hugging the wolf that the deer is watching.
a. Granny is hugging the wolf that the deer is watching.
b. Granny is hugging the wolf that is watching the deer.
c. Granny is hugging the deer that the wolf is watching.
d. Granny is hugging the deer that is watching the wolf.

APPENDIX D

Block Commander items (Chicken Licken)

Round 1
category 3
Q1 Touch the brown chicken and the yellow worm.
Q2 Touch the brown worm and the yellow chicken.
Q3 Touch the red worm and the white chicken.
Q4 Touch the white crow and the red crow.
Q5 Touch the yellow house and the red chicken.
category 4
Q6 Touch the large yellow house and the small red hammer.
Q7 Touch the small white house and the large brown hammer.
Q8 Touch the small yellow house and the large red hammer.
Q9 Remove the small brown house and the large yellow hammer.
Q10 Remove the large brown house and the large brown hammer.
category 5
Q11 Touch the brown chicken—No!—the red crow.
Q12 Remove the yellow house—No!—the brown worm.
Q13 Remove all of the worms, except for the white one.
Q14 Add all of the large houses.
Q15 Add all of the small houses, except the yellow one.
category 7
Q16 Put the small red house between the brown chicken and the yellow worm.
Q17 Put the red worm between the large brown house and the yellow chicken.
Q18 Put the small red house between the red chicken and the white worm.
Q19 Put the yellow house between the brown crow and the yellow worm.
Q20 Put the yellow worm between the brown crow and the white house.

Round 2
category 3
Q1 Touch the red chicken and the yellow plane.
Q2 Touch the red plane and the yellow chicken.
Q3 Touch the blue plane and the blue chicken.
Q4 Touch the blue plane and the red plane.
Q5 Touch the white sheep and the yellow plane.
category 4
Q6 Touch the large yellow crayon and the small red rattle.
Q7 Touch the small white crayon and the large blue rattle.
Q8 Touch the small yellow crayon and the large red rattle.
Q9 Remove the small blue crayon and the large yellow rattle.
Q10 Remove the large blue crayon and the large blue rattle.
category 5
Q11 Touch the yellow crayon—No!—the blue chicken.
Q12 Remove the red sheep—No!—the white plane.
Q13 Remove all of the crayons, except for the yellow one.
Q14 Add all of the large crayons.
Q15 Add all of the small crayons, except the blue one.
category 7
Q16 Put the small red crayon between the blue sheep and the yellow plane.

Q17 Put the red plane between the large blue crayon and the yellow chicken.
Q18 Put the small red crayon between the yellow sheep and the blue plane.
Q19 Put the yellow crayon between the blue plane and the yellow sheep.
Q20 Put the yellow sheep between the white crayon and the red plane.

Round 3
category 3
Q1 Touch the green hen and the blue mole.
Q2 Touch the green mole and the blue hen.
Q3 Touch the red duck and the blue hen.
Q4 Touch the blue mole and the red mole.
Q5 Touch the yellow gloves and the red hen.
category 4
Q6 Touch the small red gloves and the large yellow feather.
Q7 Touch the small blue gloves and the large green feather.
Q8 Touch the small yellow gloves and the large red feather.
Q9 Remove the small green gloves and the large yellow feather.
Q10 Remove the large green gloves and the large green feather.
category 5
Q11 Touch the yellow mole—No!—the red hen.
Q12 Remove the yellow gloves—No!—the green duck.
Q13 Remove all of the ducks, except for the red one.
Q14 Add all of the small gloves.
Q15 Add all of the small gloves, except the green ones.
category 7
Q16 Put the small red gloves between the green hen and the yellow duck.
Q17 Put the red duck between the large green gloves and the yellow hen.
Q18 Put the small red gloves between the yellow hen and the green duck.
Q19 Put the yellow gloves between the green mole and the yellow duck.
Q20 Put the yellow duck between the green mole and the blue gloves.

Round 4
category 3
Q1 Touch the blue chicken and the yellow fox.
Q2 Touch the blue fox and the yellow chicken.
Q3 Touch the purple fox and the green chicken.
Q4 Touch the green goose and the purple goose.
Q5 Touch the yellow leaf and the purple chicken.
category 4
Q6 Touch the large yellow leaf and the small purple acorn.
Q7 Touch the small green leaf and the large blue acorn.
Q8 Touch the small yellow leaf and the large blue acorn.
Q9 Remove the small blue leaf and the large yellow acorn.
Q10 Remove the large blue leaf and the large blue acorn.
category 5
Q11 Touch the yellow leaf—No!—the blue fox.
Q12 Remove the purple fox—No!—the green goose.
Q13 Remove all of the foxes, except for the yellow one.
Q14 Add all of the large leaves.
Q15 Add all of the small leaves, except the blue one.
category 7
Q16 Put the small purple leaf between the blue chicken and the yellow fox.
Q17 Put the purple fox between the large blue leaf and the yellow chicken.
Q18 Put the small purple leaf between the purple chicken and the green fox.
Q19 Put the yellow leaf between the blue goose and the yellow fox.
Q20 Put the yellow fox between the blue goose and the yellow leaf.

Block Commander items (Big Bad Pigs)
Round 1
category 3
Q1 Touch the brown pig and the blue bug.
Q2 Touch the brown bug and the blue pig.
Q3 Touch the pink bug and the green pig.
Q4 Touch the green baby and the pink baby.
Q5 Touch the blue radio and the pink pig.
category 4
Q6 Touch the large blue radio and the small pink vase.
Q7 Touch the small green radio and the large brown vase.
Q8 Touch the small blue radio and the large pink vase.
Q9 Remove the small brown radio and the large blue vase.
Q10 Remove the large brown radio and the large brown vase.
category 5
Q11 Touch the brown pig—No!—the pink baby.
Q12 Remove the blue radio—No!—the brown bug.
Q13 Remove all of the bugs, except for the green one.
Q14 Add all of the large radios.
Q15 Add all of the small radios, except the blue one.
category 7
Q16 Put the small pink radio between the brown pig and the blue bug.
Q17 Put the pink bug between the large brown radio and the blue pig.
Q18 Put the small pink radio between the pink pig and the green bug.
Q19 Put the blue radio between the brown baby and the blue bug.
Q20 Put the blue bug between the brown baby and the green radio.

Round 2
category 3
Q1 Touch the red pig and the brown ladder.
Q2 Touch the red ladder and thebrown pig.
Q3 Touch the blue ladder and the blue pig.
Q4 Touch the blue ladder and the red ladder.
Q5 Touch the green sheep and the brown ladder.
category 4
Q6 Touch the large brown brick and the small red bucket.
Q7 Touch the small green brick and the large blue bucket.
Q8 Touch the small brown brick and the large red bucket.
Q9 Remove the small blue brick and the large brown bucket.
Q10 Remove the large blue brick and the large blue bucket.

category 5
Q11 Touch the brown brick—No!—the blue pig
Q12 Remove the red sheep—No!—the green ladder.
Q13 Remove all of the bricks, except for the brown one.
Q14 Add all of the large bricks.
Q15 Add all of the small bricks, except the blue one.
category 7
Q16 Put the small red bricks between the blue sheep and the brown ladder.
Q17 Put the red ladder between the large blue bricks and the brown pig.
Q18 Put the small red brick between the brown sheep and the blue ladder.
Q19 Put the brown brick between the blue ladder and the brown sheep.
Q20 Put the brown sheep between the green brick and the red ladder.

Round 3
category 3
Q1 Touch the green wolf and the blue fish.
Q2 Touch the green fish and the blue wolf.
Q3 Touch the pink bug and the blue wolf.
Q4 Touch the blue fish and the pink fish.
Q5 Touch the brown brick and the pink wolf.
category 4
Q6 Touch the small pink brick and the large brown hammer
Q7 Touch the small blue brick and the large green hammer.
Q8 Touch the small yellow brick and the large pink hammer.
Q9 Remove the small green brick and the large brown hammer.
Q10 Remove the large green brick and the large green hammer.
category 5
Q11 Touch the brown fish—No!—the pinck wolf.
Q12 Remove the brown birck—No!—the green bug.
Q13 Remove all of the bugs, except for the pink one.
Q14 Add all of the small bricks.
Q15 Add all of the small bricks, except the green ones.
category 7
Q16 Put the small pinck brick between the green wolf and the brown bug.
Q17 Put the pink bug between the large green brick and the brown wolf.
Q18 Put the small pink brick between the brown wolf and the green bug.
Q19 Put the brown brick between the green fish and the brown bug.
Q20 Put the brown bug between the green fish and the blue brick.

Round 4
category 3
Q1 Touch the blue wolf and the brown sheep.
Q2 Touch the blue sheep and the brown wolf.
Q3 Touch the red sheep and the green wolf.
Q4 Touch the green pig and the red pig.
Q5 Touch the brown tomato and the red wolf.
category 4
Q6 Touch the large brown tomato and the small red egg.
Q7 Touch the small green tomato and the large blue egg.
Q8 Touch the small brown tomato r and the large blue egg.
Q9 Remove the small blue tomato and the large brown egg.
Q10 Remove the large blue tomato and the large blue egg.
category 5
Q11 Touch the brown tomato f—No!—the blue sheep.
Q12 Remove the red sheep—No!—the green pig.
Q13 Remove all of the sheep, except for the brown one.
Q14 Add all of the large tomatos.
Q15 Add all of the small tomatos, except the blue one.
category 7
Q16 Put the small red tomato between the blue wolf and the brown sheep.
Q17 Put the red sheep between the large blue tomato and the brown wolf.
Q18 Put the small red tomato between the red wolf and the green sheep.
Q19 Put the brown tomato f between the blue pig and the brown sheep.
Q20 Put the brown sheep between the blue pig and the brown tomato.

Block Commander Items (Little Red)
Round 1
category 3
Q1 Touch the brown cape and the blue socks.
Q2 Touch the brown socks and the blue cape.
Q3 Touch the red socks and the green cape.
Q4 Touch the green shoes and the red shoes.
Q5 Touch the blue basket and the red cape.
category 4
Q6 Touch the large blue basket and the small red doll.
Q7 Touch the small green basket and the large brown doll.
Q8 Touch the small blue basket and the large red doll.
Q9 Remove the small brown basket and the large blue doll.
Q10 Remove the large brown basket and the large brown doll.
category 5
Q11 Touch the brown cape—No!—the red shoes.
Q12 Remove the blue basket—No!—the brown socks.
Q13 Remove all of the socks, except for the green ones.
Q14 Add all of the large baskets.
Q15 Add all of the small baskets, except for the blue one.
category 7
Q16 Put the small red basket between the brown cape and the blue socks.
Q17 Put the red socks between the large brown basket and the blue cape.
Q18 Put the small red basket between the red cape and the green socks.
Q19 Put the blue basket between the brown shoes and the blue socks.
Q20 Put the blue socks between the brown shoes and the green basket.

Round 2
category 3
Q1 Touch the orange jacket and the grey basket.

Q2 Touch the orange basket and the grey jacket.
Q3 Touch the blue basket and the blue jacket.
Q4 Touch the blue basket and the orange basket.
Q5 Touch the green dish and the grey basket.
category 4
Q6 Touch the large grey fish and the small orange log.
Q7 Touch the small green fish and the large blue log.
Q8 Touch the small grey fish and the large orange log.
Q9 Remove the small blue fish and the large grey log.
Q10 Remove the large blue fish and the large blue log.
category 5
Q11 Touch the grey fish—No!—the blue jacket.
Q12 Remove the orange dish—No!—the green basket.
Q13 Remove all of the fish, except for the grey one.
Q14 Add all of the large fish.
Q15 Add all of the small fish, except for the blue one.
category 7
Q16 Put the small orange fish between the blue dish and the grey basket.
Q17 Put the orange basket between the large blue fish and the grey jacket.
Q18 Put the small orange fish between the grey dish and the blue basket.
Q19 Put the grey fish between the blue basket and the grey dish.
Q20 Put the grey dish between the green fish and the orange basket.
Round 3
category 3
Q1 Touch the yellow fish and the blue nightcap.
Q2 Touch the yellow nightcap and the blue fish.
Q3 Touch the pink deer and the blue fish.
Q4 Touch the blue nightcap and the pink nightcap.
Q5 Touch the red snail and the pink fish.
category 4
Q6 Touch the small pink snail and the large red boots.
Q7 Touch the small blue snail and the large yellow boots.
Q8 Touch the small red snail and the large pink boots.
Q9 Remove the small yellow snail and the large red boots.
Q10 Remove the large yellow snail and the large yellow boots.
category 5
Q11 Touch the red nightcap—No!—the pink fish.
Q12 Remove the red snail—No!—the yellow deer.
Q13 Remove all of the deer, except for the pink one.
Q14 Add all of the small snails.
Q15 Add all of the small snails, except for the green one.
category 7
Q16 Put the small pink snail between the yellow fish and the red deer.
Q17 Put the pink deer between the large yellow snail and the red fish.
Q18 Put the small pink snail between the red fish and the yellow deer.
Q19 Put the red snail between the yellow nightcap and the red deer.
Q20 Put the red deer between the yellow nightcap and the blue snail.

Round 4
category 3
Q1 Touch the yellow flowers and the brown snail.
Q2 Touch the yellow snail and the brown flowers.
Q3 Touch the grey snail and the green flowers.
Q4 Touch the green cookie and the grey cookie.
Q5 Touch the brown teapot and the grey flowers.
category 4
Q6 Touch the large brown teapot and the small grey teacup.
Q7 Touch the small green teapot and the large yellow teacup.
Q8 Touch the small brown teapot and the large yellow teacup.
Q9 Remove the small yellow teapot and the large brown teacup.
Q10 Remove the large yellow teapot and the large yellow teacup.
category 5
Q11 Touch the brown teapot—No!—the yellow snail.
Q12 Remove the grey snail—No!—the green cookie.
Q13 Remove all of the snails, except for the brown one.
Q14 Add all of the large teapots.
Q15 Add all of the small teapots, except for the yellow one.
category 7
Q16 Put the small grey teapot between the yellow flowers and the brown snail.
Q17 Put the grey snail between the large yellow teapot and the brown flowers.
Q18 Put the small grey teapot between the grey flowers and the green snail.
Q19 Put the brown teapot between the yellow cookie and the brown snail.
Q20 Put the brown snail between the yellow cookie and the brown teapot.

We claim:

1. A method on a computer for adaptively training a subject's listening comprehension using processed speech, the method comprising:

a) presenting a visual story to the subject, accompanied with an auditory narration, the auditory narration being played by the computer using a selected one of a plurality of speech processing levels;

b) presenting via the computer a plurality of questions to the subject that are related to the presented story, the plurality of questions having visual and auditory components, the auditory components using the selected one of the plurality of speech processing levels; and c) repeating a) and b) for each speech processing level within the plurality.

2. The method for adaptively training a subject's listening comprehension, as recited in claim 1 wherein the presented story is provided in a plurality of installments, each of the plurality of installments having an associated plurality of questions.

3. The method for adaptively training a subject's listening comprehension, as recited in claim 1 wherein the plurality of speech processing levels comprise 20 dB emphasis, 10 dB emphasis, or 0 dB emphasis of selected phonemes.

4. The method for adaptively training a subject's listening comprehension, as recited in claim 1 wherein b) comprises:

i) auditorily presenting via the computer a question to the subject, the question processed according to the selected one of the plurality of speech processing levels;

ii) providing a plurality of visual cards on the computer, each of the plurality of cards presenting a graphical image related to the presented visual story, one of the plurality of cards being a correct response to the presented question; and iii) repeating i) and ii) for each question in the plurality of questions.

5. The method for adaptively training a subject's listening comprehension, as recited in claim 4 wherein b) further comprises:

iv) requiring the subject to respond to each of the plurality of questions by selecting one of the plurality of visual cards.

6. The method for adaptively training a subject's listening comprehension, as recited in claim 5 further comprising:

v) incrementing a score indicator each time the subject selects the one of the plurality of cards that is a correct response to the presented question.

7. A method for training a subject's language comprehension by using an animated story presented on a computer, the animated story having visual and auditory components, the auditory components processed by the computer according to one of a plurality of speech processing levels, the method comprising:

a) providing a plurality of skill levels for training the subject, the plurality of skill levels having a plurality of questions;

b) presenting a question to the subject, from the plurality of questions, from one of the plurality of skill levels, the question having a visual component and an auditory component, the auditory component processed according to one of the plurality of speech processing levels;

c) repeating b); and d) when the subject reaches a predetermined correct response threshold, changing the speech processing level used to process the auditory component in b).

8. The method for training a subject's language comprehension, as recited in claim 7, wherein the animated story is presented to the subject prior to b).

9. The method for training a subject's language comprehension, as recited in claim 7, wherein the animated story is presented in a plurality of installments, each installment followed by b) and c).

10. The method for training a subject's language comprehension, as recited in claim 7, wherein the plurality of skill levels comprise:
   singular and plural nouns;
   singular and plural verbs;
   complex negation; and
   active and passive voice word order.

11. The method for training a subject's language comprehension, as recited in claim 7, wherein the visual component in b) comprises a plurality of cards, each of the cards having graphical components associated with the animated story, one of the cards being a correct response to the presented auditory component.

12. The method for training a subject's language comprehension, as recited in claim 7, wherein the auditory component is processed according to the same one of the plurality of speech processing levels used to process the auditory components of the animated story.

13. The method for training a subject's language comprehension, as recited in claim 7, wherein c) is repeated a plurality of times to present a plurality of questions from more than one of the plurality of skill levels.

14. The method for training a subject's language comprehension, as recited in claim 7, wherein the speech processing levels comprise 20 dB emphasis, 10 dB emphasis and 0 dB emphasis of selected phonemes.

15. The method for training a subject's language comprehension, as recited in claim 7, wherein the predetermined correct response threshold comprises 90% correct response after a predetermined number of questions, at predetermined skill levels.

16. The method for training a subject's language comprehension, as recited in claim 7, wherein when the predetermined correct response threshold is reached, the speech processing level used to process the auditory component is changed to reduce the amount of processing applied to selected phonemes.

17. The method for training a subject's language comprehension, as recited in claim 11, wherein b) further comprises:

i) requiring the subject to respond to the question by selecting one of the plurality of cards.

18. The method for training a subject's language comprehension, as recited in claim 7, further comprising:

e) when the subject reaches a predetermined correct response threshold, repeating a)–d) with a different animated story.

19. The method for training a subject's language comprehension, as recited in claim 17, wherein if the subject responds incorrectly, providing a visual indication to the subject of his/her incorrect response.

20. A method for adaptively training a subject's serial order command comprehension by using an animated story, the animated story having visual and auditory components presented by a computer, the auditory components processed according to one of a plurality of speech processing levels, the method comprising:

a) providing a plurality of categories for training the subject's serial order comprehension, the plurality of categories having a plurality of auditory commands;

b) providing a plurality of graphical objects that may be selected or manipulated by the subject, the plurality of graphical objects associated with the animated story;

c) playing one of the plurality of auditory commands, the commands processed by the computer according to one of the plurality of speech processing levels;

d) requiring the subject to select or manipulate the plurality of graphical objects according to the played one of the plurality of auditory commands; and e) repeating b)–d) to play ones of the plurality of auditory commands for each of the provided plurality of categories.

21. The method for adaptively training a subject's serial order command comprehension, as recited in claim 20, wherein the plurality of categories comprise: 1) identifying two objects with two properties each; and 2) identifying two objects with three properties each.

22. The method for adaptively training a subject's serial order command comprehension, as recited in claim 20, wherein the plurality of graphical objects are presented within a tiled grid, for each one of the played auditory commands.

23. The method for adaptively training a subject's serial order command comprehension, as recited in claim 20, wherein the one of the plurality of the speech processing levels used to process the auditory commands is equivalent to the one of the plurality of speech processing levels used to process the auditory components of the animated story.

24. The method for adaptively training a subject's serial order command comprehension, as recited in claim 20, wherein the subject selects the plurality of graphical objects by moving a cursor over ones of the plurality of graphical objects, and pressing a computer mouse.

25. The method for adaptively training a subject's serial order command comprehension, as recited in claim 20, wherein the subject manipulates the plurality of graphical objects by moving a cursor over ones of the plurality of graphical objects, pressing a computer mouse, and dragging the ones of the plurality of graphical objects.

26. A method for improving a subject's comprehension of spoken language using processed speech within a plurality of animated stories presented by a computer, the method comprising:

a) providing a plurality of audio visual games to be presented by the computer, each of the games having a plurality of auditory questions related to at least one of the plurality of animated stories, each of the plurality of auditory questions having a plurality of visual and auditory components, the auditory components processed by a plurality of speech processing levels;

b) narrating at least a portion of one of the plurality of animated stories, the narration having graphical animations, and having speech processed according to one of the plurality of speech processing levels;

c) presenting the plurality of auditory questions, via the computer for each of the plurality of audio visual games, the auditory components of the presented auditory questions processed by the computer according to the one of the plurality of speech processing levels;

d) when a subject correctly responds to the plurality of auditory questions according to a predetermined threshold, repeating b)–c) for a different one of the plurality of animated stories using a different one of the plurality of speech processing levels.

27. The method for improving a subject's comprehension of spoken language, as recited in claim 26 wherein the plurality of speech processing levels enhance the subject's ability to differentiate between similar sounding phonemes.

28. The method for improving a subject's comprehension of spoken language, as recited in claim 27 wherein the subject's ability to differentiate between the similar sounding phonemes is enhanced by amplifying selected frequency envelopes within the consonant portion of the phonemes.

29. The method for improving a subject's comprehension of spoken language, as recited in claim 26 wherein the plurality of speech processing levels comprise amplifying selected frequency envelopes within the consonant portion of selected phonemes by 20 dB, 10 dB or 0 dB.

\* \* \* \* \*